(12) United States Patent
Hood et al.

(10) Patent No.: US 8,810,417 B2
(45) Date of Patent: Aug. 19, 2014

(54) BEVERAGE IMMERSATE WITH DETECTION CAPABILITY

(75) Inventors: Leroy E. Hood, Seattle, WA (US);
Edward K. Y. Jung, Bellevue, WA (US);
Elizabeth A. Sweeney, Seattle, WA (US); Clarence T. Tegreene, Bellevue, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 1081 days.

(21) Appl. No.: 12/584,054

(22) Filed: Aug. 28, 2009

(65) Prior Publication Data
US 2011/0053283 A1    Mar. 3, 2011

Related U.S. Application Data

(63) Continuation-in-part of application No. 12/584,055, filed on Aug. 28, 2009.

(51) Int. Cl.
*G08B 21/00* (2006.01)
*G01N 33/14* (2006.01)

(52) U.S. Cl.
CPC .................................. *G01N 33/14* (2013.01)
USPC ............. 340/603; 340/618; 340/620; 702/22; 436/104; 422/68.1; 73/61.43; 73/426; 99/285

(58) Field of Classification Search
USPC ......... 340/618, 573.3, 539, 603, 620; 702/22; 422/68.1; 73/61.43, 426; 436/104; 99/279, 285
See application file for complete search history.

(56) References Cited

U.S. PATENT DOCUMENTS

| | | | |
|---|---|---|---|
| 4,275,083 A | 6/1981 | Colten et al. | |
| 4,843,830 A * | 7/1989 | Haul | 62/59 |
| 5,174,962 A | 12/1992 | Brennan | |
| 5,183,740 A | 2/1993 | Ligler et al. | |
| 5,303,585 A | 4/1994 | Lichte | |
| 5,354,654 A | 10/1994 | Ligler et al. | |

(Continued)

FOREIGN PATENT DOCUMENTS

| | | |
|---|---|---|
| EP | 1 397 997 A1 | 3/2004 |
| WO | WO 99/31560 | 6/1999 |
| WO | WO 2007/113727 A2 | 10/2007 |
| WO | WO 2008/006152 A1 | 1/2008 |

OTHER PUBLICATIONS

Abràmoff, Michael D., et al.; "Image Processing with ImageJ"; Biophotonics International; Bearing a date of Jul. 2004; pp. 36-42; The British Library.

(Continued)

*Primary Examiner* — Hoi Lau
(74) *Attorney, Agent, or Firm* — Dorsey & Whitney LLP

(57) ABSTRACT

Methods and systems described herein include beverage immersates and methods of their use. Systems include: at least one beverage immersate, wherein the at least one beverage immersate includes at least one sensor configured to detect at least one analyte in a fluid within a personal use beverage container; and at least one signal transmitter configured to transmit a signal responsive to the at least one beverage immersate. Methods include: detecting one or more analyte in fluid within a personal use beverage container with at least one sensor integral to at least one beverage immersate; and communicating data from the at least one beverage immersate to at least one device external to the beverage immersate.

54 Claims, 12 Drawing Sheets

(56) References Cited

U.S. PATENT DOCUMENTS

| | | | |
|---|---|---|---|
| 5,360,819 A | 11/1994 | Giese | |
| 5,475,096 A | 12/1995 | Gold et al. | |
| 5,516,931 A | 5/1996 | Giese et al. | |
| 5,571,401 A | 11/1996 | Lewis et al. | |
| 5,602,273 A | 2/1997 | Giese et al. | |
| 5,604,104 A | 2/1997 | Giese et al. | |
| 5,610,020 A | 3/1997 | Giese et al. | |
| 5,631,146 A | 5/1997 | Szostak et al. | |
| 5,661,039 A | 8/1997 | Kung et al. | |
| 5,762,939 A | 6/1998 | Smith et al. | |
| 5,804,563 A | 9/1998 | Still et al. | |
| 5,807,758 A | 9/1998 | Lee et al. | |
| 5,831,012 A | 11/1998 | Nilsson et al. | |
| 6,022,326 A | 2/2000 | Tatum et al. | |
| 6,102,872 A | 8/2000 | Doneen et al. | |
| 6,163,248 A | 12/2000 | Paek et al. | |
| 6,187,599 B1 | 2/2001 | Asher et al. | |
| 6,214,546 B1 | 4/2001 | Asher et al. | |
| 6,255,461 B1 | 7/2001 | Mosbach et al. | |
| 6,258,870 B1 | 7/2001 | Hubbell et al. | |
| 6,310,105 B1 | 10/2001 | Damodaran | |
| 6,372,248 B1 | 4/2002 | Qin et al. | |
| 6,397,190 B1 | 5/2002 | Goetz | |
| 6,467,333 B2 | 10/2002 | Lewis et al. | |
| 6,468,223 B2 | 10/2002 | Kaga | |
| 6,491,643 B2 | 12/2002 | Katzman et al. | |
| 6,528,954 B1 | 3/2003 | Lys et al. | |
| 6,544,800 B2 | 4/2003 | Asher | |
| 6,558,320 B1 | 5/2003 | Causey, III et al. | |
| 6,609,068 B2 | 8/2003 | Cranley et al. | |
| 6,623,698 B2 | 9/2003 | Kuo | |
| 6,635,452 B1 | 10/2003 | Monforte et al. | |
| 6,670,427 B1 | 12/2003 | Ulbricht et al. | |
| 6,746,529 B1 | 6/2004 | Witteveen et al. | |
| 6,753,191 B2 | 6/2004 | Asher et al. | |
| 6,754,472 B1 | 6/2004 | Williams et al. | |
| 6,797,522 B1 | 9/2004 | Still et al. | |
| 6,821,331 B2 | 11/2004 | Damodaran | |
| 6,949,347 B2 | 9/2005 | Singh et al. | |
| 6,953,589 B1 | 10/2005 | Trautman et al. | |
| 7,022,514 B2 | 4/2006 | Vodyanoy et al. | |
| 7,105,352 B2 | 9/2006 | Asher et al. | |
| 7,247,489 B2 | 7/2007 | Bakker et al. | |
| 7,288,415 B2 | 10/2007 | Huang | |
| 7,292,349 B2 | 11/2007 | Miller et al. | |
| 7,314,453 B2 | 1/2008 | Kuo | |
| 7,402,423 B2 | 7/2008 | Taghizadeh et al. | |
| 7,442,754 B2 | 10/2008 | Tepper et al. | |
| 7,459,713 B2 | 12/2008 | Coates | |
| 7,483,805 B2 | 1/2009 | Sparks et al. | |
| 7,555,437 B2 | 6/2009 | Pierce | |
| 7,563,026 B2 | 7/2009 | Mandelkern et al. | |
| 7,576,319 B2 | 8/2009 | Miller et al. | |
| 7,647,237 B2 | 1/2010 | Malave et al. | |
| 7,722,536 B2 | 5/2010 | Goodnow | |
| 7,736,310 B2 | 6/2010 | Taub | |
| 7,766,658 B2 | 8/2010 | Tricca et al. | |
| 7,813,780 B2 | 10/2010 | Shah et al. | |
| 7,860,727 B2 | 12/2010 | Showalter et al. | |
| 8,241,575 B2 | 8/2012 | Murray et al. | |
| 2002/0044891 A1 | 4/2002 | Miller et al. | |
| 2002/0127143 A1 | 9/2002 | Kuo | |
| 2003/0022225 A1 | 1/2003 | Monforte et al. | |
| 2003/0023189 A1 | 1/2003 | Kuo | |
| 2003/0034895 A1* | 2/2003 | Reich | 340/618 |
| 2003/0062909 A1 | 4/2003 | Liao | |
| 2003/0138939 A1 | 7/2003 | Vodyanoy et al. | |
| 2003/0143580 A1 | 7/2003 | Straus | |
| 2004/0006257 A1 | 1/2004 | Burch et al. | |
| 2004/0018508 A1 | 1/2004 | Friedman | |
| 2004/0078219 A1 | 4/2004 | Kaylor et al. | |
| 2004/0100376 A1 | 5/2004 | Lye et al. | |
| 2004/0115132 A1 | 6/2004 | Young et al. | |
| 2004/0162467 A1 | 8/2004 | Cook | |
| 2005/0037112 A1* | 2/2005 | Daley et al. | 426/104 |
| 2005/0143787 A1 | 6/2005 | Boveja et al. | |
| 2006/0033631 A1* | 2/2006 | Cupples et al. | 340/612 |
| 2006/0204444 A1 | 9/2006 | Young et al. | |
| 2006/0292174 A1 | 12/2006 | de los Rios et al. | |
| 2007/0021458 A1 | 1/2007 | Ishikawa et al. | |
| 2007/0059245 A1 | 3/2007 | Young et al. | |
| 2007/0190084 A1 | 8/2007 | Hilt et al. | |
| 2007/0254260 A1 | 11/2007 | Alden, IV et al. | |
| 2008/0102953 A1 | 5/2008 | Schultz | |
| 2008/0175963 A1 | 7/2008 | Pope | |
| 2008/0265146 A1 | 10/2008 | Coates | |
| 2008/0294061 A1 | 11/2008 | Wang et al. | |
| 2008/0300569 A1* | 12/2008 | Schateikis et al. | 604/403 |
| 2008/0303678 A1* | 12/2008 | McCredy | 340/628 |
| 2009/0120038 A1 | 5/2009 | Abercrombie, III et al. | |
| 2009/0149988 A1 | 6/2009 | Hyde et al. | |
| 2009/0170124 A1 | 7/2009 | Campbell | |
| 2009/0247857 A1 | 10/2009 | Harper et al. | |
| 2010/0089152 A1 | 4/2010 | Kolada et al. | |
| 2011/0053283 A1* | 3/2011 | Hood et al. | 436/104 |
| 2011/0054801 A1 | 3/2011 | Hilborne et al. | |

OTHER PUBLICATIONS

Alexeev, Vladimir L., et al.; "Photonic Crystal Glucose-Sensing Material for Noninvasive Monitoring of Glucose in Tear Fluid"; Clinical Chemistry; Bearing a date of 2004; pp. 2353-2360; vol. 50, No. 12; American Association for Clinical Chemistry.

Asher Research Group; "Colloid Group"; Printed on Jul. 31, 2009; pp. 1-14; located at http://www.pitt.edu/~asher/homepage/colgrp.html.

Baker, Brian R., et al.; "An Electronic, Aptamer-Based Small-Molecule Sensor for the Rapid, Label-Free Detection of Cocaine in Adulterated Samples and Biological Fluids"; Journal of the American Chemical Society; Bearing a date of Feb. 18, 2006; pp. 3138-3139; vol. 128; American Chemical Society.

Baker, Monya; "From The Lab: Biotechnology; Beaming Biodata: Mutation detection goes wireless"; MIT Technology Review; Bearing a date of May 2005; pp. 1-5.

Balon, Helena R., et al.; "Society of Nuclear Medicine Procedure Guideline for C-14 Urea Breath Test"; Society of Nuclear Medicine Procedure Guidelines Manual; Bearing a date of Jun. 2002; pp. 37-39.

Bauer, Susan; "Saliva spits out information on chemical exposure"; PNNL News Release; Bearing a date of Oct. 24, 2003; Printed on Jul. 31, 2009; pp. 1-2; located at http://www.innovations-report.com/html/reports/life_sciences/report-22741.html.

Ben-Moshe, Matti, et al.; "Fast Responsive Crystalline Colloidal Array Photonic Crystal Glucose Sensors"; Analytical Chemistry; Bearing a date of Jul. 15, 2006; pp. 5149-5157; vol. 78, No. 14; American Chemical Society.

Besanger, Travis R., et al.; "Screening of Inhibitors Using Enzymes Entrapped in Sol—Gel-Derived Materials"; Analytical Chemistry; Bearing a date of May 15, 2003; pp. 2382-2391; vol. 75, No. 10; American Chemical Society.

Biohesion Incorporated; "Advanced Surface Binding Technology"; Bearing a date of 2007; p. 1 of 1; located at http://www.biohesion.com/.

Boisen, Anja, et al.; "Rapid molecular detection of food- and water-borne diseases"; Microbiology Today; Bearing a date of Aug. 2007; pp. 116-118.

Bromberg, Lev; "Intelligent Polyelectrolytes and Gels in Oral Drug Delivery"; Current Pharmaceutical Biotechnology; Bearing a date of 2003; pp. 339-349; vol. 4, No. 5; Bentham Science Publishers Ltd.

Bruno, John G., et al.; "Use of Magnetic Beads in Selection and Detection of Biotoxin Aptamers by Electrochemiluminescence and Enzymatic Methods"; BioTechniques; Bearing a date of Jan. 2002; pp. 178-183; vol. 32, No. 1.

Byrne, Mark E., et al.; "Molecular imprinting within hydrogels"; Advanced Drug Delivery Reviews; Bearing a date of 2002; pp. 149-161; vol. 54; Elsevier Science B.V.

Chen, Chao-Tsen, et al.; "Fluorescent, Sequence-Selective Peptide Detection by Synthetic Small Molecules"; Science; Bearing a date of Feb. 6, 1998; pp. 851-853; vol. 279.

(56) References Cited

OTHER PUBLICATIONS

Daunert, Sylvia, et al.; "Genetically Engineered Whole-Cell Sensing Systems: Coupling Biological Recognition with Reporter Genes"; Chemical Reviews; Bearing a date of 2000; pp. 2705-2738; vol. 100, No. 7; American Chemical Society.

Dill, Kilian, et al.; "Immunoassays and sequence-specific DNA detection on a microchip using enzyme amplified electrochemical detection"; Journal of Biochemical and Biophysical Methods; Bearing a date of 2004; pp. 181-187; vol. 59; Elsevier B.V.

Drafts, Bill; "Acoustic Wave Technology Sensors"; Sensors; Bearing a date of Oct. 1, 2000; Printed on Jul. 31, 2009; pp. 1-9; located at http://www.sensorsmag.com/articles/1000/68/main.shtml.

Drummond, T Gregory, et al.; "Electrochemical DNA sensors"; Nature Biotechnology; Bearing a date of Oct. 2003; pp. 1192-1199; vol. 21, No. 10; Nature Publishing Group.

Dwarakanath, Sulatha, et al.; "Quantum dot-antibody and aptamer conjugates shift fluorescence upon binding bacteria"; Biochemical and Biophysical Research Communications; Bearing a date of 2004; pp. 739-743; vol. 325; Elseveir Inc.

Ehrick, Jason D., et al.; "Genetically engineered protein in hydrogels tailors stimuli-responsive characteristics"; Nature Materials; Bearing a date of Apr. 2005; pp. 298-302; vol. 4; Nature Publishing Group.

Gao, Liang, et al.; "Design and Characterization of a Multisource Hand-Held Tandem Mass Spectrometer"; Analytical Chemistry; Bearing a date of Oct. 1, 2008; pp. 7198-7205; vol. 80, No. 19; American Chemical Society.

Garrison, Kenneth E., et al.; "A review of membrane sampling from biological tissues with applications in pharmacokinetics, metabolism and pharmacodynamics"; European Journal of Pharmaceutical Sciences; Bearing a date of 2002; pp. 1-12; vol. 17; Elsevier Science B.V.

Gelfand, Alexander; "Device Offers a Roadside Dope Test"; MIT Technology Review; Bearing a date of Aug. 4, 2009; pp. 1-4.

Gonzalez, Anjelica L., et al.; "Integrin Interactions with Immobilized Peptides in Polyethylene Glycol Diacrylate Hydrogels"; Tissue Engineering; Bearing a date of 2004; pp. 1775-1786; vol. 10, No. 11/12.

Hagleitner, C., et al.; "Smart single-chip gas sensor microsystem"; Nature; Bearing a date of Nov. 15, 2001; pp. 293-296; vol. 414; Macmillan Magazines Ltd.

Heim, Sarah J.; "Lab on a Swab"; MIT Technology Review; Bearing a date of Aug. 29, 2005; pp. 1-4; located at http://www.technologyreview.com/biomedicine/14709/.

Heine, R. Phillip, et al.; "Accuracy of salivary estriol testing compared to traditional risk factor assessment in predicting preterm birth"; American Journal of Obstetrics and Gynecology; Bearing a date of Jan. 1999; pp. 214S-218S; vol. 180(IS-111).

Herber, Sebastiaan, et al.; "A hydrogel-based CO2 sensor"; MESA+ Institute for Nanotechnology, University of Twente; Bearing a date of Aug. 29, 2005; Printed on Jul. 31, 2009; pp. 1-2; located at http://bios.ewi.utwente.nl/research/electrochemicalsystems/formeranalysissystemsandsensorsprojects/ahydrogelbased.doc/index.html.

Hitachi, Ltd.; "Development of world's first RFID sensor chip for DNA analysis"; Press Release; Bearing a date of Feb. 10, 2005; pp. 1-4.

Hodinka, R. L., et al.; "Detection of Human Immunodeficiency Virus Antibodies in Oral Fluids"; Clinical and Diagnostic Laboratory Immunology; Bearing a date of Jul. 1998; pp. 419-426; vol. 5, No. 4; American Society for Microbiology.

Hofman, Lindsay F.; "Human Saliva as a Diagnostic Specimen"; Journal of Nutrition; Bearing a date of 2001; pp. 1621S-1625S; vol. 131; American Society for Nutritional Sciences.

Holtz, John H., et al.; "Polymerized colloidal crystal hydrogel films as intelligent chemical sensing materials"; Nature; Bearing a date of Oct. 23, 1997; pp. 829-832; vol. 389; Macmillan Publishers Ltd.

Horner, Scott R., et al.; "A proteomic biosensor for enteropathogenic E. coli"; Biosensors and Bioelectronics; Bearing a date of 2006; pp. 1659-1663; vol. 21; Elsevier B.V.

Indo-Asian News Service; "Scientists develop biosensor to detect E. coli bacteria"; RxPG News; Bearing dates of Feb. 25, 2006 and Aug. 19, 2006; Printed on Jul. 31, 2009; pp. 1-3; located at http://www.rxpgnews.com/article_3524.shtml.

Karjalainen, S., et al.; "Salivary Cholesterol of Healthy Adults in Relation to Serum Cholesterol Concentration and Oral Health"; Journal of Dental Research; Bearing a date of Oct. 1997; pp. 1637-1643; vol. 76, No. 10; Sage Publications.

Katagiri, Kiyofumi, et al.; "Creation of asymmetric bilayer membrane on monodispersed colloidal silica particles"; Colloids and Surfaces B: Biointerfaces; Bearing a date of 2004; pp. 149-153; vol. 38; Elsevier B.V.

Kaufman, Eliaz, et al.; "The Diagnostic Applications of Saliva—A Review"; Critical Reviews in Oral Biology & Medicine; Bearing a date of 2002; pp. 197-212; vol. 13, No. 2.

Kharitonov, Sergei A., et al.; "Exhaled Markers of Pulmonary Disease"; American Journal of Respiratory and Critical Care Medicine; Bearing a date of 2001; pp. 1693-1722; vol. 163.

Khurana, Surender, et al.; "Antigenic Fingerprinting of H5N1 Avian Influenza Using Convalescent Sera and Monoclonal Antibodies Reveals Potential Vaccine and Diagnostic Targets"; PLoS Medicine; Bearing a date of Apr. 2009; pp. 1-13; vol. 6, No. 4.

Kimo Instruments; "Hand-held carbon dioxide (CO2) analyzer, CO, CO2, ° C., %HR"; Printed on Aug. 27, 2009; pp. 1; located at http://www.directindustry.com/prod/kimo/hand-held-carbon-dioxide-co2-analyzer-11846-389510.html.

Korsman, Stephen; "Chapter 6: Vaccines"; Influenza Report 2006 Edited by Kamps et al.; Bearing a date of 2006; pp. 1-4, and 127-149; Flying Publisher.

Kumar, Ashok; "Biosensors Based on Piezoelectric Crystal Detectors: Theory and Application"; JOM-e; Bearing a date of Oct. 2000; Printed on Jul. 31, 2009; pp. 1-9; vol. 52, No. 10; located at http://www.tms.org/pubs/journals/JOM/0010/Kumar/Kumar-0010.html.

Lai, Rebecca Y., et al.; "Aptamer-Based Electrochemical Detection of Picomolar Platelet-Derived Growth Factor Directly in Blood Serum"; Analytical Chemistry; Bearing a date of Jan. 1, 2007; pp. 229-233; vol. 79, No. 1; American Chemical Society.

Lai, Rebecca Y., et al.; "Differential Labeling of Closely Spaced Biosensor Electrodes via Electrochemical Lithography"; Langmuir; Bearing a date of 2006; pp. 1932-1936; vol. 22; American Chemical Society.

Lakshmi, Dhana, et al.; "Electrochemical Sensor for Catechol and Dopamine Based on a Catalytic Molecularly Imprinted Polymer-Conducting Polymer Hybrid Recognition Element"; Analytical Chemistry; Bearing a date of May 1, 2009; pp. 3576-3584; vol. 81, No. 9; American Chemical Society.

Lavigne, John J., et al.; "Solution-Based Analysis of Multiple Analytes by a Sensor Array: Toward the Development of an 'Electronic Tongue'"; Journal of the American Chemical Society; Bearing a date of Jul. 1998; pp. 6429-6430; vol. 120; American Chemical Society.

Lawrence, Herenia P.; "Salivary Markers of Systemic Disease: Noninvasive Diagnosis of Disease and Monitoring of General Health"; Journal of the Canadian Dental Association; Bearing a date of Mar. 2002; pp. 170-174; vol. 68, No. 3.

Lee, Jeong-O, et al.; "Aptamers as molecular recognition elements for electrical nanobiosensors"; Analytical and Bioanalytical Chemistry; Bearing a date of 2008; pp. 1023-1032; vol. 390; Springer-Verlag.

Lempert, Phil; "Digital house calls? Check your health at home"; MSNBC.com; Bearing a date of Feb. 21, 2006; p. 1 of 1; located at http://www.msnbc.msn.com/id/11476436/.

Li, Y., et al.; "The Oral Fluid MEMS/NEMS Chip (OFMNC): Diagnostic & Translational Applications"; Advances in Dental Research; Bearing a date of 2005; pp. 3-5; vol. 18; Sage.

Liu, Chung-Chiun; "Applications of Microfabrication Techniques in Electrochemical Sensor Development"; Applied Biochemistry and Biotechnology; Bearing a date of 1993; pp. 99-107; vol. 41; The Humana Press Inc.

Liu, Ke, et al.; "Detection of $Pb^{2+}$ Using a Hydrogel Swelling Microcantilever Sensor"; Analytical Sciences; Bearing a date of Jan. 2004; pp. 9-11; vol. 20; The Japan Society for Analytical Chemistry.

(56) References Cited

OTHER PUBLICATIONS

MiScope Handheld Digital Microscope; "Description"; Forensics Source; Printed on Aug. 27, 2009; pp. 1; located at http://www.forensicssource.com/p-1810-miscope-handheld-digital-microscope.aspx.
Miyata, Takashi, et al.; "A reversibly antigen-responsive hydrogel"; Nature; Bearing a date of Jun. 24, 1999; pp. 766-769; vol. 399; Macmillan Magazines Ltd.
Miyawaki, Atsushi, et al.; "Fluorescent indicators for $Ca^{2+}$ based on green fluorescent proteins and calmodulin"; Nature; Bearing a date of Aug. 28, 1997; pp. 882-887; vol. 388; Macmillan Publishers Ltd.
Moldoveanu, Z., et al.; "Human immune responses to influenza virus vaccines administered by systemic or mucosal routes"; Vaccine; Bearing a date of 1995; pp. 1006-1012; vol. 13, No. 11; Elsevier Science Ltd.
Murthy, S. Narasimha, et al.; "Physical and Chemical Permeation Enhancers in Transdermal Delivery of Terbutaline Sulphate"; AAPS PharmSciTech; Bearing a date of 2001; pp. 1-5; vol. 2, No. 1.
Musa-Veloso, Kathy, et al.; "Breath acetone is a reliable indicator of ketosis in adults consuming ketogenic meals"; The American Journal of Clinical Nutrition; Bearing a date of 2002; pp. 65-70; vol. 76; American Society for Clinical Nutrition.
Nishanian, Parunag, et al.; "Oral Fluids as an Alternative to Serum for Measurement of Markers of Immune Activation"; Clinical and Diagnostic Laboratory Immunology; Bearing a date of Jul. 1998; pp. 507-512; vol. 5, No. 4; American Society for Microbiology.
Overhoff Technology Corporation; "All Purpose, Affordable, Beta/Gamma Meter With A Sensitivity to 1 μR/h!; Ion Ferret Gamma/Beta Detector Ionization Chamber/Survey Meter"; Printed on Aug. 27, 2009; pp. 1-2.
Pathak, C.M., et al.; "Urea Breath Test for *Helicobacter pylori* Detection: Present Status"; Tropical Gastroenterology; Bearing a date of Oct.-Dec. 2004; pp. 156-161; vol. 25, No. 4.
Peppas, Nicholas A., et al.; "Polymers and Gels as Molecular Recognition Agents"; Pharmaceutical Research; Bearing a date of May 2002; pp. 578-587; vol. 19, No. 5; Plenum Publishing Corporation.
Potter, Steve M., et al.; "A new approach to neural cell culture for long-term studies"; Journal of Neuroscience Methods; Bearing a date of 2001; pp. 17-24; vol. 110; Elsevier Science B.V.
Queyras, Armelle, et al.; "Non-invasive techniques for analysing hormonal indicators of stress"; Annali dell'Istituto Superiore di Sanita; Bearing a date of 2004; pp. 211-221; vol. 40, No. 2.
Quickmedical Medical Equipment and Supplies; "AlcoHawk CA2000—Premium Digital Alcohol Breath Analyzer"; Printed on Jul. 31, 2009; pp. 1-4; located at http://www.quickmedical.com/breathalyzer/alcoscan_tech.html.
Quickmedical Medical Equipment and Supplies; "Digital Alcohol Breathalyzer—AlcoHawk ABI Premium"; Printed on Jul. 31, 2009; pp. 1-3; located at http://www.quickmedical.com/breathalyzer/alcoscan.html.
Rädler, Ulf, et al.; "Design of Supported Membranes Tethered via Metal-Affinity Ligand-Receptor Pairs"; Biophysical Journal; Bearing a date of Dec. 2000; pp. 3144-3152; vol. 79; Biophysical Society.
Rider, Todd H., et al.; "A B Cell-Based Sensor for Rapid Identification of Pathogens"; Science; Bearing a date of Jul. 11, 2003; pp. 213-215; vol. 301.
Savran, Cagri A., et al.; "Micromechanical Detection of Proteins Using Aptamer-Based Receptor Molecules"; Analytical Chemistry; Bearing a date of Jun. 1, 2004; pp. 3194-3198; vol. 76, No. 11; American Chemical Society.
Science Daily; "Salivary Diagnostics, The 'Magic Mirror' to Your Health . . . At Your Personal Computer"; Bearing a date of Apr. 5, 2008; pp. 1-2; located at http://www.sciencedaily.com/releases/2008/04/080405095750.htm.
Şenel, Sevda, et al.; "Drug permeation enhancement via buccal route: possibilities and limitations"; Journal of Controlled Release; Bearing a date of 2001; pp. 133-144; vol. 72; Elsevier Science B.V.
Skelley, Alison M., et al.; "Development and evaluation of a microdevice for amino acid biomarker detection and analysis on Mars"; PNAS; Bearing a date of Jan. 25, 2005; pp. 1041-1046; vol. 102, No. 4; The National Academy of Sciences of the USA.
Snow, E. S., et al.; "Chemical Detection with a Single-Walled Carbon Nanotube Capacitor"; Science; Bearing a date of Mar. 25, 2005; pp. 1942-1945; vol. 307.
Sotiropoulou, Sofia, et al.; "Stabilization of enzymes in nanoporous materials for biosensor applications"; Biosensors and Bioelectronics; Bearing a date of 2005; pp. 1674-1679; vol. 20; Elsevier B.V.
SPI Pharma Group; "New Formulation Makes Gum Delivery System Efficient and Affordable"; Special Delivery: The quarterly newsletter from SPI Pharma Group; Bearing a date of Summer 2001; pp. 1-4.
Stojanovic, Milan N., et al.; "Aptamer-Based Folding Fluorescent Sensor for Cocaine"; Journal of the American Chemical Society; Bearing a date of 2001; pp. 4928-4931; vol. 123, No. 21; American Chemical Society.
Tanaka, Toyoichi, et al.; "Polymer Gels that can Recognize and Recover Molecules"; Faraday Discussions; Bearing a date of 1996; pp. 201-206; vol. 102.
Tolosa, Leah, et al.; "Lifetime-Based Sensing of Glucose Using Energy Transfer with a Long Lifetime Donor"; Analytical Biochemistry; Bearing a date of 1997; pp. 102-108; vol. 250; Academic Press.
Tombelli, Sara, et al.; "Piezoelectric biosensors: Strategies for coupling nucleic acids to piezoelectric devices"; Methods; Bearing a date of 2005; pp. 48-56; vol. 37; Elsevier Inc.
U.S. Department of Energy, Office of Environmental Management, Office of Science and Technology; "Innovative Technology Summary Report, Lumi-Scint Liquid Scintillation Counter"; Bearing a date of Jul. 2001; Four pages plus pp. 1-24.
U.S. Department of Health and Human Services, Centers for Disease Control and Prevention, National Center for Health Statistics; Table 3, Table 4 and Table V from "Summary Health Statistics for U.S. Adults: National Health Interview Survey, 2003"; Bearing a date of Jul. 2005; pp. 1-4, 20-23, and 112-113.
U.S. Department of Health and Human Services, Centers for Disease Control and Prevention, National Center for Health Statistics; Table 1 from "Summary Health Statistics for U.S. Children: National Health Interview Survey, 2003"; Bearing a date of Mar. 2005; pp. 1-4, and 8-9.
Utada, A. S., et al.; "Monodisperse Double Emulsions Generated from a Microcapillary Device"; Science; Bearing a date of Apr. 22, 2005; pp. 537-541; vol. 308.
Vamvakaki, Vicky, et al.; "Fluorescence detection of enzymatic activity within a liposome based nano-biosensor"; Biosensors and Bioelectronics; Bearing a date of 2005; pp. 384-388; vol. 21; Elsevier B.V.
Vass, Géza, et al.; "Comparison of Nasal and Oral Inhalation during Exhaled Breath Condensate Collection"; American Journal of Respiratory and Critical Care Medicine; Bearing a date of 2003; pp. 850-855; vol. 167.
Vital Sensors Technologies LLC; "VS-1000B Series Inline Brix Sensors for the Beverage Industry; Inline Networked Smart Infrared Sensors for Real-Time Process Monitoring: Continuous Accurate Brix measurement of Regular and Diet Beverages"; Bearing a date of 2008; pp. 1-4.
Walker, Richard F., et al.; "Radioimmunoassay of Progesterone in Saliva: Application to the Assessment of Ovarian Function"; Clinical Chemistry; Bearing a date of 1979; pp. 2030-2033; vol. 25, No. 12.
Wee, Kyung Wook, et al.; "Novel electrical detection of label-free disease marker proteins using piezoresistive self-sensing micro-cantilevers"; Biosensors and Bioelectronics; Bearing a date of 2005; pp. 1932-1938; vol. 20; Elsevier B.V.
Wikipedia; "Taste"; Bearing a date of May 19, 2009; printed on May 22, 2009; pp. 1-10; located at http://en.wikipedia.org/wiki/Taste.
Win, Maung Nyan, et al.; "Codeine-binding RNA aptamers and rapid determination of their binding constants using a direct coupling surface plasmon resonance assay"; Nucleic Acids Research; Bearing a date of 2006; pp. 5670-5682; vol. 34, No. 19.
Wong, David T.; "Oral Fluid NanoSensor Test (OFNASET)"; Bearing a date of Sep. 1, 2006; located at http://www.researchgrantdatabase.com/g/5U01DE017790-03/Oral-Fluid-NanoSensor-Test-OFNASET/ [Abstract Only].

(56) References Cited

OTHER PUBLICATIONS

Wong, David T.; "Salivary diagnostics powered by nanotechnologies, proteomics and genomics"; Journal of the American Dental Association; Bearing a date of 2006; pp. 313-321; vol. 137; American Dental Association.

Yazawa, Yoshiaki, et al.; "A Wireless Biosensing Chip for DNA Detection"; 2005 IEEE International Solid-State Circuits Conference, Session 30, Displays and Biosensors, 30.6; Bearing a date of 2005; pp. 562-563, and 617.

Ye, Lei, et al.; "Molecularly imprinted polymers as antibody and receptor mimics for assays, sensors and drug discovery"; Analytical and Bioanalytical Chemistry; Bearing a date of 2004; pp. 1887-1897; vol. 378.

Yoon, Min-Sung, et al.; "Characterisation of advanced glycation endproducts in saliva from patients with diabetes mellitus"; Biochemical and Biophysical Research Communications; Bearing a date of 2004; pp. 377-381; vol. 323; Elsevier Inc.

Yusa, Go, et al.; "Controlled multiple quantum coherences of nuclear spins in a nanometre-scale device"; Nature; Bearing a date of Apr. 21, 2005; pp. 1001-1005; vol. 434; Nature Publishing Group.

U.S. Appl. No. 12/657,166, Hood et al.

U.S. Appl. No. 12/584,055, Hood et al.

U.S. Appl. No. 12/584,364, Hood et al.

Balmaseda, Angel, et al.; "Diagnosis of Dengue Virus Infection by Detection of Specific Immunoglobulin M (IgM) and IgA Antibodies in Serum and Saliva"; Clinical and Diagnostic Laboratory Immunology; Bearing a date of Mar. 2003; pp. 317-322; vol. 10, No. 2; American Society for Microbiology.

Barnes, Allan J., et al.; "Excretion of Methamphetamine and Amphetamine in Human Sweat Following Controlled Oral Methamphetamine Administration"; Clinical Chemistry; Bearing a date of 2008; pp. 172-180; vol. 54, No. 1; American Society for Clinical Chemistry.

Beck, M., et al.; "Nanoelectrochemical transducers for (bio-) chemical sensor applications fabricated by nanoimprint lithography"; Microelectronic Engineering; Bearing a date of 2004; pp. 837-842; vol. 73-74; Elsevier B.V.

Cramer, Joyce A., et al.; "Compliance With Medication Regimens for Mental and Physical Disorders"; Psychiatric Services; Bearing a date of Feb. 1998; pp. 196-201; vol. 49; American Psychiatric Association.

Davis, Mark D.P., et al.; "Thermoregulatory Sweat Testing in Patients With Erythromelalgia"; Archives of Dermatology; Bearing a date of Dec. 2006; pp. 1583-1588; vol. 142; American Medical Association; located at www.archdermatol.com.

Hemmingsson, Tryggve, et al.; "Novel Hand-Held Device for Exhaled Nitric Oxide-Analysis in Research and Clinical Applications"; Journal of Clinical Monitoring and Computing; Bearing a date of 2004; pp. 379-387; vol. 18; Springer 2005.

Huestis, Marilyn A., et al.; "Excretion of $\Delta^9$-Tetrahydrocannabinol in Sweat"; Forensic Science International; Bearing a date of Jan. 30, 2008; pp. 173-177 (pp. 1-10); vol. 174(2-3); National Institutes of Health.

Illigens, Ben M.W., et al.; "Sweat testing to evaluate autonomic function"; Clinical Autonomic Research; Bearing a date of Nov. 6, 2008; pp. 79-87; vol. 19.

Kintz, Pascal, et al.; "Sweat testing for heroin and metabolites in a heroin maintenance program"; Clinical Chemistry; Bearing a date of 1997; pp. 736-739; vol. 43, No. 5.

Knott, Christine, et al.; "Phenytoin-valproate interaction: importance of saliva monitoring in epilepsy"; British Medical Journal; Bearing a date of Jan. 2, 1982; pp. 13-16; vol. 284.

Kovacs, Eva M.R., et al.; "Effect of caffeinated drinks on substrate metabolism, caffeine excretion, and performance"; Journal of Applied Physiology; Bearing a date of 1998; pp. 709-715; vol. 85; American Physiological Society.

Lavrik, Nickolay V., et al.; "Cantilever transducers as a platform for chemical and biological sensors"; Review of Scientific Instruments; Bearing a date of Jul. 2004; pp. 2229-2253; vol. 75, No. 7; American Institute of Physics.

Mezzasoma, Letizia, et al.; "Antigen Microarrays for Serodiagnosis of Infectious Diseases"; Clinical Chemistry; Bearing a date of 2002; pp. 121-130; vol. 48, No. 1; American Association of Clinical Chemistry.

Mitchell, Alex J., et al.; "Why don't patients take their medicine? Reasons and solutions in psychiatry"; Advances in Psychiatric Treatment; Bearing a date of 2007; pp. 336-346; vol. 13.

Patel, Nilay; "Nintendo Wii Vitality Sensor detects your pulse"; Engadget; Bearing a date of Jun. 2, 2009; Printed on Jan. 8, 2010; pp. 1-24; located at: http://www.engadget.com/2009/06/02/nintendo-wii-vitality-sensor-detects-your-pulse/.

Phillips, Michael; "Sweat-Patch Test for Alcohol Consumption: Rapid Assay with an Electrochemical Detector"; Alcoholism: Clinical and Experimental Research; Bearing a date of Fall 1982; pp. 532-534; vol. 6, No. 4; The American Medical Society on Alcoholism, The Research Society on Alcoholism, and the National Council on Alcoholism.

Potyrailo, Radislav A., et al.; "Chemical Sensors Based on Micromachined Transducers with Integrated Piezoresistive Readout"; Analytical Chemistry; Bearing a date of Aug. 15, 2006; pp. 5633-5638; vol. 78, No. 16; American Chemical Society.

Robroeks, C.M.H.H.T., et al.; "Exhaled nitric oxide and biomarkers in exhaled breath condensate indicate the presence, severity and control of childhood asthma"; Clinical and Experimental Allergy; Bearing a date of 2007; pp. 1303-1311; vol. 37; Blackwell Publishing Ltd.

Schena, Mark, et al.; "Quantitative Monitoring of Gene Expression Patterns with a Complementary DNA Microarray"; Science; Bearing a date of Oct. 20, 1995; pp. 467-470; vol. 270.

Smith, Andrew D., et al.; "Use of Exhaled Nitric Oxide Measurements to Guide Treatment in Chronic Asthma"; The New England Journal of Medicine; Bearing a date of May 26, 2005; pp. 2163-2173; vol. 352, No. 21; Massachusetts Medical Society.

Tang, Dianping, et al.; "Magnetic Control of an Electrochemical Microfluidic Device with an Arrayed Immunosensor for Simultaneous Multiple Immunoassays"; Clinical Chemistry; Bearing a date of 2007; pp. 1323-1329; vol. 53, No. 7; American Association for Clinical Chemistry.

Thieme, Thomas, et al.; "Determination of Measles, Mumps, and Rubella Immunization Status Using Oral Fluid Samples"; JAMA; Bearing a date of Jul. 20, 1994; pp. 219-221; vol. 272, No. 3.

Uchida, Hideaki, et al.; "A New Assay Using Surface Plasmon Resonance (SPR) to Determine Binding of the *Lactobacillus acidophilus* Group to Human Colonic Mucin"; Bioscience, Biotechnology, and Biochemistry; Bearing a date of 2004; pp. 1004-1010; vol. 68, No. 5.

\* cited by examiner

FIG. 2
Fig. 2A
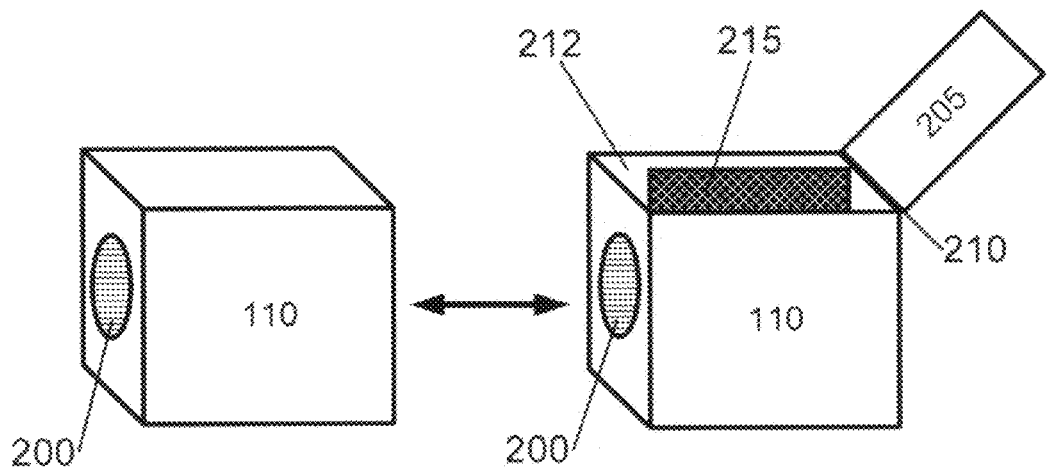
Fig. 2B
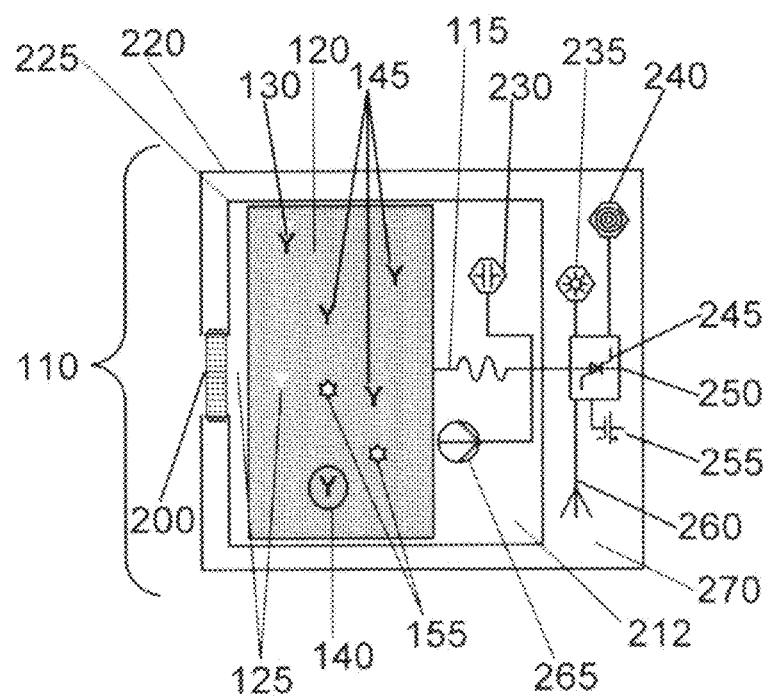

FIG. 3
Fig. 3A
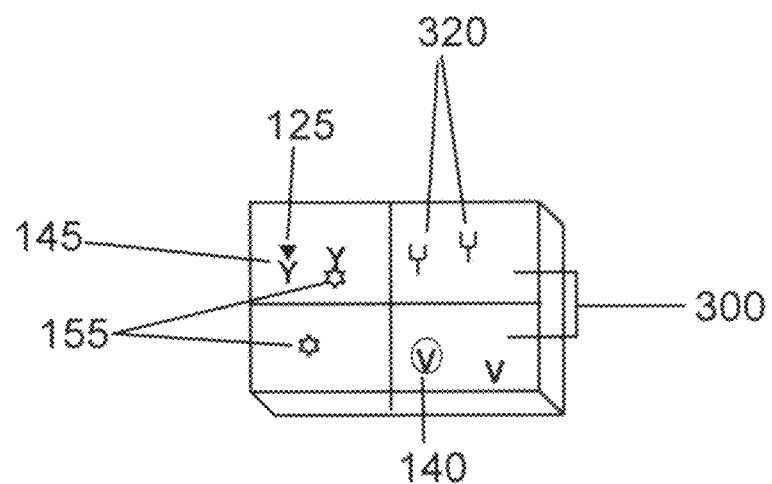
Fig. 3B
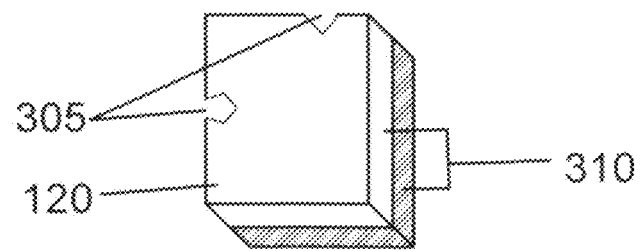

FIG. 5
Fig. 5A
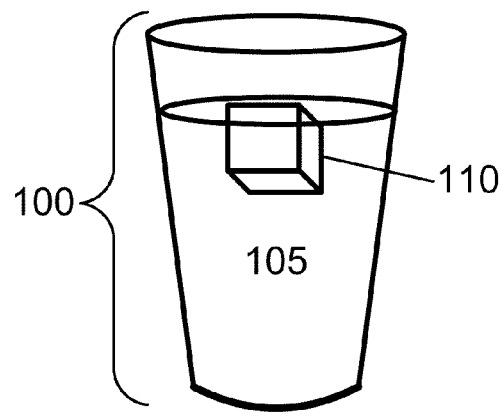
Fig. 5B
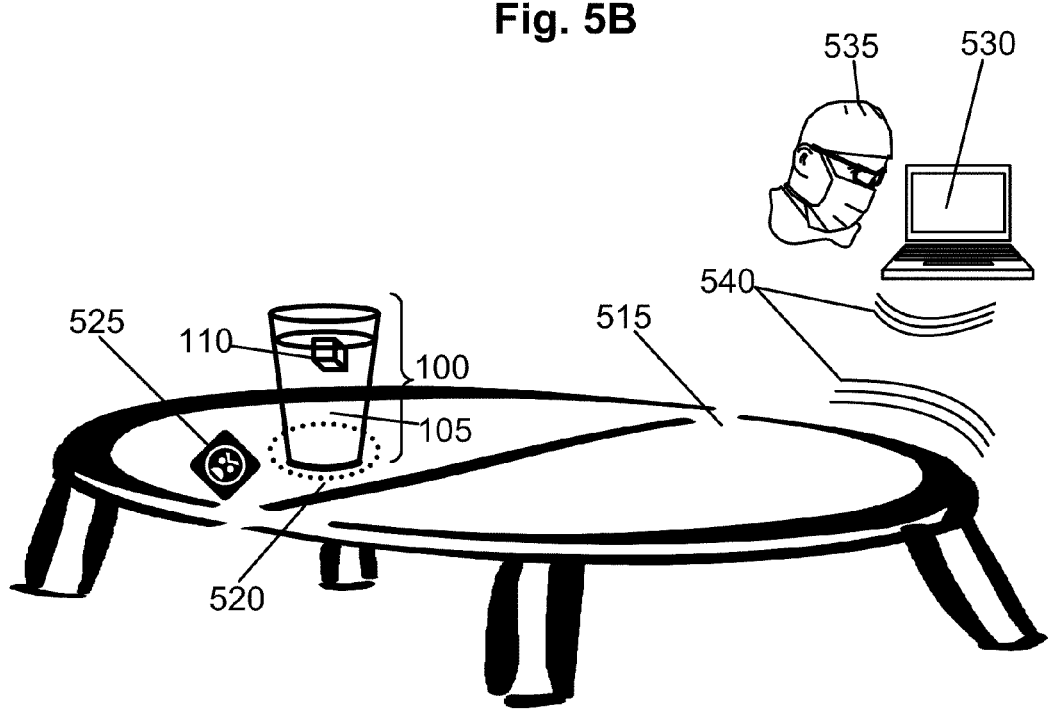

US 8,810,417 B2

BEVERAGE IMMERSATE WITH DETECTION CAPABILITY

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 12/584,055, titled DEVICES AND METHODS FOR DETECTING AN ANALYTE IN SALIVARY FLUID, naming Leroy E. Hood, Edward K. Y. Jung, Elizabeth A. Sweeney, Clarence T. Tegreene, and Lowell L. Wood, Jr. as inventors, filed Aug. 28, 2009, which is currently co-pending, or is an application of which a currently co-pending application is titled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

SUMMARY

In one aspect, a system includes, but is not limited to, at least one beverage immersate, wherein the at least one beverage immersate includes: at least one sensor configured to detect at least one substance in a fluid within a personal use beverage container; and at least one signal transmitter configured to transmit a signal responsive to the at least one sensor. In one aspect, a system includes, but is not limited to: at least one beverage immersate, wherein the at least one beverage immersate includes at least one sensor configured to detect at least one substance in a fluid within a personal use beverage container; and at least one detection device including at least one port configured to communicate with the at least one beverage immersate. In addition to the foregoing, other system aspects are described in the claims, drawings, and text forming a part of the present disclosure.

In one aspect, a method includes, but is not limited to, a method of detecting one or more substance in fluid, including: detecting one or more substance in fluid within a personal use beverage container with at least one sensor integral to at least one beverage immersate; and communicating data from the at least one beverage immersate to at least one device external to the beverage immersate. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In addition to the foregoing, various other method and/or system and/or program product aspects are set forth and described in the teachings such as text (e.g., claims and/or detailed description) and/or drawings of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

BRIEF DESCRIPTION OF THE FIGURES

FIG. 2A is a schematic of some aspects of a beverage immersate.

FIG. 2B is a schematic of a cross-section view of a beverage immersate.

FIG. 3A is a schematic of modules of a beverage immersate.

FIG. 3B is a schematic of modules of a beverage immersate.

FIG. 5A is a schematic of some aspects of a beverage immersate system.

FIG. 5B is a schematic of a cross-section view of a beverage immersate system.

DETAILED DESCRIPTION

Figure 1:
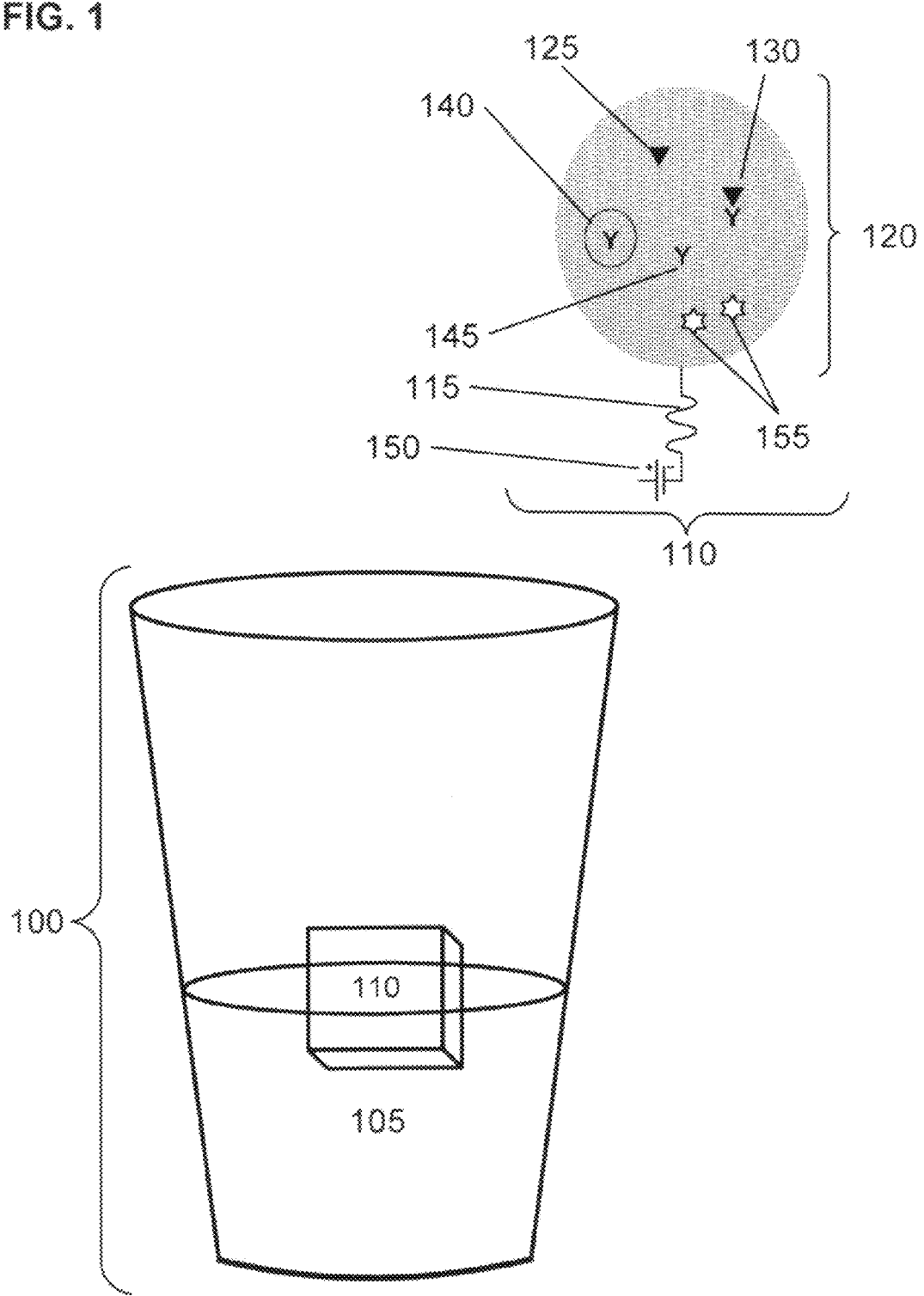
FIG. 1 is a schematic of some aspects of a beverage immersate.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

With reference now to FIG. 1, shown is an example of a system for detecting one or more substance, such as an analyte, in fluid within an individual-use beverage container that may serve as context for introducing one or more processes and/or devices described herein. The use of the same symbols in different drawings typically indicates similar or identical items. FIG. 1 shows an embodiment of a system wherein a personal-use drinking vessel 100 contains a beverage fluid 105 and a beverage immersate 110. A "personal use beverage container" or an "individual use drinking vessel" as used herein refers to a beverage container configured for use by a single individual for their personal beverage consumption. A beverage container includes any individual-use drinking vessel. For example, in some embodiments the beverage container may be a cup, mug, glass, carton or can configured for individual use and beverage consumption by a particular person. In some embodiments, the beverage container may include at least one attached straw or other drinking enhancement attachment. The beverage container may include a lid or cover, which may include a specific region configured for drinking. A beverage container may include one or more discrete regions configured for drinking. A beverage container may include one or more discrete regions configured to facilitate consumption of a beverage by an individual user. The beverage container may be disposable, or it may be reusable, such as after cleaning. The beverage container may be reusable, such as with modular components that are replaceable, rechargeable, swappable, or exchangeable. A beverage container is configured to contain a beverage during consumption by an individual user, and may also be configured to store the beverage for some period of time. For example, a bottle or can may be configured for an individual to drink directly from the bottle or can, and beverage may also be stored within these types of containers.

A "beverage immersate," as used herein, refers to a discrete device configured for entire or partial immersion in a beverage fluid within a personal-use beverage container, which may be a single-use beverage container. A beverage immersate is sized and configured for entire or partial immersion in a beverage fluid without significantly hindering the use of the personal-use beverage container for drinking by an individual user. An "individual user," as used herein, refers to an individual using a personal-use beverage container containing at least one beverage immersate for drinking. In some contexts, an "individual user" may be synonymous with a "user" or a "person" as used herein. A beverage immersate may sink or float in the beverage fluid, and may be either partially or completely submerged in the beverage fluid at any given time. A beverage immersate may come into contact with the beverage for an extended period of time, such as hours or days, and remain in the beverage during consumption of the beverage by an individual user. A beverage immersate may be located within a beverage fluid in an individual-use drinking vessel while an individual is actively drinking from the vessel. A beverage immersate may be configured for inclusion in a beverage container for the duration of the container's use by an individual drinking the beverage. A beverage immersate may have modular components. A beverage immersate may be reusable with components that are replaceable and/or rechargeable. A beverage immersate may include at least one component that is encapsulated or within an emulsion, such as a component configured for timed release or durability during storage.

A beverage immersate may have decorative or esthetic characteristics, such as being configured to appear like an ice cube, a flower, an ornament or other decorative appearance designed to please a user. A beverage immersate may include functional lights, as described herein, but may also include lights, such as colored lights, that are designed to be ornamental or provide amusement to an individual user. A beverage immersate may include marks, colors, logos, symbols or lettering to distinguish a specific beverage immersate. For example, a beverage immersate may be marked with an individual user's initials or name. For example, a beverage immersate may be marked with a company logo, trademark, brand, or tradename. A beverage immersate may be personalized or customized for a specific individual using the beverage immersate. A beverage immersate may include circuitry configured to elicit changes in the appearance of the beverage immersate in response to a signal from external instrumentation, such as a cell, phone, laptop or personal digital assistant (PDA) or an external device such as those described herein. For example, a beverage immersate may include circuitry and lights configured to change the appearance of the beverage immersate in response to a signal from external instrumentation, such as by blinking, changing the color of the lights illuminated, or changing the combination of lights illuminated. See, for example, International Patent Application No. WO 99/31560 to Mueller et al., titled "Digitally controlled illumination methods and systems" which is herein incorporated by reference. Changes in appearance of a beverage immersate may be personalized or customized to an individual user of the beverage immersate.

A beverage immersate may be manufactured in part or entirety from a substantially rigid material, for example a hard plastic or fibrous composite. A beverage immersate may include one or more material configured to contribute to the mass of the beverage immersate in its entirety. For example, a beverage immersate may be configured to sink or float in a particular beverage at a particular temperature and at standard atmospheric pressures. A beverage immersate may be configured with a specific gravity or relative density appropriate to a given embodiment. For example, a beverage immersate may contain an enclosed air bubble configured to maintain buoyancy of the beverage immersate in a beverage. For example a beverage immersate may include sufficient materials denser than water to decrease buoyancy of a beverage immersate, configured to result in the beverage immersate sinking below the surface of the beverage. A beverage immersate may be configured to change density relative to a liquid, such as a beverage immersate including an enclosed air bubble for buoyancy wherein the air bubble enclosure is not sealed completely, allowing leakage of bubbles over time. Such bubbles may add visual effect or amusement aspects as well as changing buoyancy of the beverage immersate over time.

A "beverage," as used herein, refers to any fluid generally prepared, purified or processed with a goal of consumption by an individual through drinking. An "individual user," as used herein, includes an individual human user as well as an individual domesticated animal, for example an individual dog, cat, goat, cow or sheep. For example, a beverage may include water, juices, dairy products, alcoholic beverages, chemical compositions, medicinal compositions, nutritional compositions, and other fluids as well as mixtures of these drinks. A beverage may include sugar-based sweeteners, such as glucose, as well as non sugar-based sweeteners such as aspartame, saccharin, sucralose, or stevioside. A beverage may contain non-fluid particulates such as undissolved material, contaminants, or food additives such as those based on agar, tapioca or gelatin. A beverage may include additives such as vitamins, minerals, or other nutrients. A beverage may include additives such as flavor enhancers. A beverage may include additives such as fillers or diluents. A beverage may be carbonated. A beverage may be dispensed into a beverage container in a formulation or composition ready for drinking by an individual. For example, juice may be poured directly from a storage container into a glass configured for an individual to drink out of directly. More than one beverage component may be mixed together, either directly before adding to a beverage container, or within a beverage container. For example, milk or cream may be mixed directly with tea in a cup configured for an individual user to drink from directly. A beverage may be heated or cooled to be suitable for drinking, for example a beverage may be chilled in a refrigeration unit, may have ice added, may be heated, or may be mixed with a warmer fluid. For example, hot coffee may be chilled or have ice added to create iced coffee, or coffee which is no longer at a desired warm temperature may have additional and warmer coffee added to increase the temperature of the beverage. Depending on the embodiment, a beverage immersate may be added to a beverage fluid when the beverage is in its consumption state, such as after mixing, heating, or chilling of the beverage fluid, or it may be included prior to or during mixing, heating, or cooling of the beverage fluid. Therefore a particular beverage immersate may be configured to be operable in these different conditions or in a range of conditions.

Although a human individual user is envisioned, it is also envisioned that the systems and methods described herein may be utilized with other animals, for example domesticated animals such as canines, felines, bovines, or equines. For example, the beverage immersate depicted herein may be configured for immersion in an individual-use beverage container configured for use by a domestic house cat or a domestic dog, for example in a water dish, bowl, or bottle. For example, the beverage immersate depicted herein may be configured for immersion in an individual-use beverage container configured for use by a goat, sheep or cow, for example a bottle with an attached straw or hose configured for drinking. Systems and methods such as those described herein may be used to monitor the health and well-being of domestic animals, such as through the analysis of stress hormones present in salivary fluids. See, for example, Queyras and Carosi, "Non-invasive techniques for analyzing hormonal indicators of stress," *Ann Ist Super Sanita,* 40(2): 211-221 (2004), which is incorporated herein by reference. Systems and methods such as those described herein may be used to monitor the health and well-being of domestic animals, such as through the analysis of contaminants, pathogens, allergens, antibiotics, pesticides, herbicides, or additives in beverages, including water, intended for drinking by domestic animals.

A beverage immersate includes at least one sensor configured to detect at least one substance in a fluid within a personal use beverage container. A fluid includes a beverage fluid, which includes the constituent fluid of a beverage. A fluid includes salivary fluid. During the act of drinking, a beverage fluid and salivary fluid often become mixed in an individual's oral cavity and adjacent areas so that the fluid in a personal use beverage container may contain a mixture of fluids originally arising from the individual user's oral cavity and the beverage fluid itself. "Salivary fluid," as used herein, includes saliva and related fluids. Related fluids include, for example, blood, breath condensate, oral gas, crevicular fluid, transudate, exudate, gingival crevicular fluid, mucosal transudate or exudate, ingested remnants and mucus, which are collectively referred to herein as "salivary fluid." See, for example, Vass et al., "Comparison of nasal and oral inhalation during exhaled breath condensate collection," *Am J Respir Crit Care Med* 167: 850-855 (2003), which is herein incorporated by reference. Salivary fluids may, in some situations, provide a noninvasive source for biomarkers of systemic and local diseases and disorders. In some individuals, such as children and the infirm, saliva may be preferable to samples taken invasively. See, for example, European Patent Application No. 02019770 to Gröschl and Rauh titled "Detection device," and U.S. Pat. No. 6,022,326 to Tatum et al., titled "Device and method for automatic collection of whole saliva," which are herein incorporated by reference. Studies illustrate the numbers and varieties of substances, including analytes, that are available for testing in salivary fluids. See, for example: Kaufman and Lamster, "The Diagnostic Applications of Saliva-A Review", *Crit Rev Oral Biol Med,* 13(2): 197-212 (2002); Lawrence, "Salivary markers of systemic disease: noninvasive diagnosis of disease and monitoring of general health," *J. Can. Dent. Assoc.* 68(3): 170-174 (2002); Li et al., "The oral fluid MEMS/NEMS chip (OFMNC): diagnostic and translational applications," *Adv. Dent. Res.,* 18: 3-5 (2005); "Salivary diagnostics, the 'magic mirror' to your health . . . at your personal computer," *ScienceDaily,* Apr. 5, 2008; and Wong, "Salivary Diagnostics Powered by Nanotechnologies, Proteomics and Genomics," *J Am Dent Assoc.,* 137:313-321 (2006) which are herein incorporated by reference. In addition to compounds associated with the mouth and mucous membranes, such as immunoglobulin A (IgA), other substances can be present at detectable levels, including markers of disease, drugs and alcohol. For example, salivary fluid has been used as a medium for the detection of HIV antibodies. See Hodinka et al., "Minireview: Detection of Human Immunodeficiency Virus antibodies in oral fluids," *Clin. & Diagn. Lab Immun.,* 5(4): 419-426 (1998), and Nishanian et al., "Oral fluids as an alternative to serum for measurement of markers of immune activation," *Clin. & Diagn. Lab Immun.,* 5(4): 507-512 (1998), which are herein incorporated by reference. Markers related to systemic health have also been measured in salivary fluids as an alternative source to serum. Hormones, antibodies, electrolytes, and cholesterol are just a few of the substances that can be monitored in salivary fluids. See, for example: Hofman, "Human saliva as a diagnostic specimen," *Journal of Nutrition,* 131: 1621S-1625S (2001); Wong, "Oral Fluid NanoSensor Test (OFNASET)" grant 5U01DE017790-03 grant abstract; Karjalainen et al., "Salivary cholesterol of healthy adults in relation to serum cholesterol concentration and oral health," *J. Dent. Res.* 76: 1637-1643 (1997); and Queyras and Carosi, "Non-invasive techniques for analyzing hormonal indicators of stress," *Ann Ist Super Sanita,* 40(2): 211-221 (2004), which are incorporated herein by reference. Studies have also shown that substances that are markers of environmental chemical exposure are detectable in salivary fluids. See for example, Bauer "Saliva spits out information on chemical exposure," *Innovations Report,* Oct. 24, 2003, which is herein incorporated by reference. Some substances, including analytes, in salivary fluids arise from gingival crevicular fluids, transudates or exudates.

A substance, as used herein, includes a component of the fluid within the personal use beverage container which may be of interest or concern to some users of the beverage immersate. A substance, as used herein, includes a contaminant or ingredient of the fluid that may be harmful or perceived as harmful by one or more users of the beverage immersate. A substance, as used herein, includes an additive or component originally arising from the beverage fluid that may be perceived as desirable or undesirable by one or more individual users of the beverage immersate. For example, a substance may include glucose in a beverage, which may be undesirable for ingestion by individuals such as diabetics or persons following some diet regimens. For example, a substance may include one or more contaminants, such as pesticides, drugs, residues or salts that may be undesirable to one or more persons using a beverage immersate. For example, a substance may include a microbe, for example a pathogenic microbe contaminating the beverage. For example, a substance may include one or more medical agent or medicinal additive. A substance may include a taggant, including a taggant bound to one or more agent or material that may be of interest to some users of a beverage immersate. A substance may include at least one of a biological marker, an antibody, a polypeptide, a protein, a complex, a nucleic acid, a cell, a pathogen, a lipid, an alcohol, a sterol, a carbohydrate, a metal, an electrolyte, a metabolite, an organic compound, an organophosphate, a drug, a therapeutic, a gas, or a pollutant. A substance may include one or more substance that is a marker or hallmark of a fluid of interest. For example, pH may be a marker for citrus juice inclusion. For example, glucose or fructose may be a hallmark of total sugar content. For example, a specific microbial protein may be a marker for the microbe as a whole.

The beverage immersate may be customized for an individual user, such as through modular units, and a substance may be specifically of interest to that individual user or a group of similar individual users. For example, a diabetic individual may be specifically concerned about glucose, sugars generally, carbohydrates, or related substances. For example, a person with allergies may be concerned about the presence of specific allergenic substances. For example, an individual following an organic diet may be concerned about pesticide or herbicide residues. For example, a person scheduled to ingest a particular medicinal agent may wish to confirm that the medicinal agent is present in the beverage. For example, a person on a particular medical regimen may wish to confirm that no contraindicated substances are present in the beverage before drinking. For example, grapefruit juice is contraindicated for people prescribed a number of medications, including amiodarone, buspirone, carbamezapine, cyclosporine, felodipine, saquinavir, simvastin and lovastatin. A beverage immersate may be customized or personalized for an individual user or a group of users through the inclusion of specific modular units, such as sensor units configured to detect specific substances.

A substance may be the byproduct of a process used to manufacture the beverage fluid or a substance may originate as an additive to the beverage fluid. A substance may include an analyte, for example an analyte may originate in salivary fluid of a person using a personal use drinking vessel and be incorporated into the fluid in the vessel through the process of drinking. A substance may include at least one biological marker, antibody, polypeptide, protein, complex, nucleic acid, cell, pathogen, lipid, alcohol, sterol, carbohydrate, metal, electrolyte, organic compound, nonorganic compound, organophosphate, drug, therapeutic, gas, or pollutant. A substance, such as an analyte, may be the result of a bioprocess, a chemical process, or a natural process. The presence of one or more substance, such as an analyte, may alone or in combination be an indicator of a physiologic state, a disease state like an active infection, or a metabolic state in a person drinking from the vessel. A substance, such as an analyte, may include a metabolite. For example the presence of the analyte acetone may operate as an indicator of ketosis. See, for example, Musa-Veloso et al., "Breath acetone is a reliable indicator of ketosis in adults consuming ketogenic meals," *Am J Clin Nutr.* 76(1):65-70 (2002), and Khartinov and Barnes, "Exhaled Markers of Pulmonary Disease," *Am J Respir Crit Care Med,* 163:1693-1722 (2001), and U.S. Pat. No. 6,609,068 to Cranley et al., titled "Personal computer breath analyzer for health-related behavior modification and method," which are herein incorporated by reference. For example, the presence of unusual levels of pepsin activity may indicate the presence of gastroesophageal reflux disease (GERD). See, for example, U.S. Pat. No. 7,402,423 to Taghizadeh, titled "Apparatus for detection of pepsin," which is hereby incorporated by reference. An analyte may include at least one metabolite. For example, an analyte may include a metabolic product generated by the physiology of the user. A metabolite may include a type that is indicative of a metabolic state, for example a metabolite may be indicative of a healthy state, or a disease state. A metabolite may include a type that is indicative of a physiological state. In some embodiments, the system may include at least one provided agent, such as a drug or compound that may be metabolized by the user. A system wherein the analyte includes at least one metabolite may also include at least one provided agent, wherein the at least one metabolite includes at least one metabolite of the provided agent. For example, the beverage immersate may release a provided agent into the beverage fluid and the substance detected may be a metabolite of the provided agent. For example, a system user may ingest a provided agent and the sensor may be configured to detect a metabolite of the provided agent.

As illustrated in FIG. 1, a beverage immersate 110 includes at least one sensor configured to detect at least one substance in a fluid within a personal use beverage container. A "sensor" as used herein, includes a unit that specifically identifies a substance, such as an analyte, and generates a signal that the identification has been made. A sensor may include a gas or chemical sensor, or an optical, acoustic, or electric sensor. A sensor may be an electrochemical sensor. A sensor may be a biological sensor. The signal generated by a sensor may be, for example, an electrical, visual, magnetic, acoustic, vibrational, heat, light (including infrared (IR) or ultraviolet (UV)), radio frequency (RF) or electromagnetic radiation signal. At least one sensor integral to the beverage immersate is configured to detect at least one substance in a fluid within an individual-use beverage container. A sensor may recognize one or more substance. A sensor may be configured to detect at least one substance in a beverage fluid. A sensor may be configured to detect at least one substance in salivary fluid, such as salivary fluid that has mixed into a beverage fluid while an individual user is drinking. A sensor may be configured to detect at least one substance in an additive or contaminant of the fluid, such as a contaminant diffusing into the fluid from the residue on the surface of the container itself, or an additive originating from a component of the fluid.

One or more sensor is configured to be included within a beverage immersate. Depending on the embodiment, many possible types and configurations of the one or more sensor integral to beverage immersate may be utilized, including one or more array. Depending on the embodiment, a sensor may be utilized that is very small, such as a sensor or array that is configured to fit within the beverage immersate. In some embodiments, the sensor is a chemical sensor. See, for example, Snow et al., "Chemical Detection with a Single-Walled Carbon Nanotube Capacitor," *Science* 307:1942-1945 (2005), which is incorporated herein by reference. A sensor incorporated within a beverage immersate should be of a size and shape able to be configured for complete enclosure within the beverage immersate. Furthermore, a sensor incorporated within a beverage immersate should be operable at appropriate temperatures and conditions, such as pH and the presence of carbonation, present in the relevant beverage. Some types and configurations of sensors, therefore, are not suitable for inclusion within beverage immersates configured for use in certain fluids. An external detection device may be configured to detect at least one signal from the beverage immersate, such as from the sensor. For example, a detection device may include at least one port for communication with the beverage immersate that includes one or more instruments for detection of a signal from the sensor integral to the beverage immersate. For example, a detection device that includes at least one port for communication with the beverage immersate may include one or more instruments for detection of a signal from the beverage immersate, such as a signal emitted by a signal emitter integral to the beverage immersate.

Depending on the embodiment, sensor types may include gas sensors, "electronic nose" sensors, "electronic tongue" sensors, conductive-polymer gas-sensors (chemoresistors), nuclear magnetic resonance imagers, cantilevers, aptimer-based sensors, volumetric sensors, or capillary electrophoretic devices. See, for example: U.S. Pat. No. 5,303,585 to Lichte, titled "Fluid Volume Sensor;" Hagleitner et al., "Smart single-chip gas sensor microsystem," Nature 414: 293-296 (2001); Yusa et al., "Controlled multiple quantum coherences of nuclear spins in a nanometer-scale device," Nature 434:1001-1005 (2005); U.S. Pat. No. 5,174,962 to Brennan titled "Apparatus for determining DNA sequences by mass spectrometry;" and Skelley et al., "Development and evaluation of a microdevice for amino acid biomarker detection and analysis on Mars," Proc. Natl. Acad. Sci. USA, 102 (4):1041-1046 (2005), which are herein incorporated by reference. See, for example, Lavigne et al., "Solution-based analysis of multiple analytes by a sensor array: toward the development of an "electronic tongue," Journal of the Americal Chemical Society, 120: 6429-6430 (1998), which is herein incorporated by reference. See, for example, US Patent Application No. 2007/0021458 to Ishikawa et al., titled "Selective resonance of bodily agents," and Li et al., "The oral fluid MEMS/NEMS chip (OFMNC): diagnostic and translational applications," Adv. Dent. Res., 18: 3-5 (2005), which are herein incorporated by reference. The at least one sensor may be configured to be indirectly responsive to an analyte. For example, a sensor may be configured to be responsive to a metabolite of an analyte. For example, a sensor may be configured to be responsive to a taggant, which may be configured to be detectable in the presence of one or more substance. For example, a sensor may be configured to be responsive to a taggant bound to a substance.

A sensor may include at least one matrix 120 configured for specific binding or retention of a substance 125. The matrix 120 may be configured to bind or retain the substance directly, or it may include one or more recognition element 145. A recognition element 145 is configured to specifically recognize and retain the substance 125, as illustrated 130. A recognition element may chemically recognize one or more substance. A recognition element may recognize one or more substance, for example through physical or chemical interactions. A recognition element may bind one or more substance, such as through physical association or chemical association. In some embodiments, the recognition element may be encapsulated 140 prior to contact with the fluid, such as to maintain a stable conformation of the recognition element prior to use. For example, the recognition element may be encapsulated in one or more carbohydrates, oils, lipids, microspheres, nanospheres or gum materials. The recognition element may be covered by an emulsion. The encapsulation or emulsion of a recognition element may be configured to dissipate, dissolve or be dispersed through contact with a fluid or a substance. See, for example, U.S. Pat. No. 6,746,529 to Wittevenn et al., titled "Stable, spray-dried composition in a carbohydrate substrate and process for obtaining said composition," which is herein incorporated by reference. In some embodiments, a beverage immersate 110 may include one or more taggant 155, which may be retained in a matrix. A sensor may be configured to respond to one or more taggant. A sensor may include retaining materials, such as a proteoglycan or a charged polymer such as polylysine. Other retaining materials could be included in the sensor, such as semi-specific or non-specific adsorbents, such a silica ($SiO_2$) or alumina ($Al_2O_3$)— containing gel or an ion exchange resin, including as part of the matrix 120. A sensor may also include structural material, such as non-reactive gels, plastics or composites configured to shape, enclose or structurally support other components of the sensor, including a matrix.

A matrix 120 might include one or more gel, like a hydrogel, a hydrosol, a sol-gel, a xerogel, an aerogel, a hydrocarbon gel, a natural polymer gel, a synthetic polymer gel, a ferrogel, a colloid, a responsive gel, a superporous hydrogel or microparticle gel. One or more portion of a sensor may be in a dehydrated form prior to use. For example, a matrix may be in a dehydrated form prior to contact with fluid, such as salivary fluid or beverage fluid. Many types of porous hydrogels may be utilized, such as those used in the wound dressing described in U.S. Pat. No. 6,372,248, to Qin et al, titled "Dehydrated Hydrogels," which is incorporated herein by reference. A matrix may include a hydrogel including hybrid materials, for example a hydrogel containing a hybrid protein-polysaccharide material. See U.S. Pat. No. 6,821,331 to Damodaran, titled "Protein-polysaccharide hybrid hydrogels," which is herein incorporated by reference. The matrix may be a natural material-based gel like agarose, a natural and/or synthetic polymer gel, hydrogel, or colloid, and may include a gum base such as an acacia gum. See, for example, U.S. Pat. No. 7,022,514 to Vodyanoy et al., titled "Use of acacia gum to isolate and preserve biological material," and US Patent Application No. 2003/0138939 A1 to Vodyanoy et al., titled "Use of acacia gum to isolate and preserve biological material," which are incorporated herein by reference. A matrix may, instead or in addition, be configured as a lipid monolayer or bilayer, as in a micelle or liposome, and may be anchored to a vessel wall through a nonorganic tether. See, for example, "Design of Supported Membranes Tethered via Metal-Affinity Ligand-Receptor Pairs," Rädler et al., Biophysical Journal 79:3144-3152 (2000), which is herein incorporated by reference. A matrix may be configured as one or more film or layer. A matrix may include at least one of a hydrogel, hydrosol, sol-gel, xerogel, aerogel, hydrocarbon gel, natural polymer gel, synthetic polymer gel, superporous gel, ferrogel, lipid, colloid, encapsulation or emulsion. The matrix may include an absorbent, like cotton, cellulose, natural or artificial sponge. The matrix may include one or more gel, such as a hydrogel, a hydrosol, a sol-gel, a xerogel, an aerogel, a hydrocarbon gel, a natural polymer gel, a synthetic polymer gel, a ferrogel, a colloid, a responsive gel, a superporous hydrogel or microparticle gel. A matrix may be configured as a plurality of spheres, such as micro- or nanospheres. Such spheres may include protein cages, liposomes, synthetic hybrid cerasomes, microspheres or nanospheres of one or more natural and/or synthetic polymer, including dendrimers. See, for example, Katagiri et al. "Creation of asymmetric bilayer membrane on monodispersed colloidal silica particles," *Colloids Surf B Biointerface,* 38(3-4):149-53 (2004), which is incorporated herein by reference. For example, a matrix may include at least one ligand affinity resin with or without a recognition element, such as a conjugated peptide or antibody, such as those that are commonly used in chromatography and purification. For example, a matrix may include at least one ionophore as a recognition element presented on microspheres within the matrix. See, for example, U.S. Pat. No. 7,247,489 to Bakker, titled "Ion detecting microspheres and methods of use thereof," which is incorporated herein by reference. For example, distinctly from a recognition element configured as a separate agent, a recognition element may be a recognition site molecularly imprinted within a matrix itself or a part thereof, such as a molecular mimetic. See, for example: U.S. Pat. No. 6,670,427 to Ulbricht et al., titled "Template-textured materials, methods for the production and use thereof;" Ye et al., "Molecularly imprinted polymers as antibody and receptor mimics for assays, sensors and drug discovery;" *Anal Bioanal Chem.* 378(8):1887-1897 (2004); and Peppas et al., "Polymers and gels as molecular recognition agents," *Pharm Res.* 19(5):578-587 (2002), which are incorporated herein by reference.

A sensor may include a recognition element, such as illustrated as 145 in FIG. 1, configured to recognize a substance 125. A recognition element may specifically identify and bind a substance such as illustrated 130. A recognition element may chemically recognize one or more substance. For example, a recognition element may include a peptide chain such as described in U.S. Pat. No. 7,402,423 to Taghizadeh, titled "Apparatus for the detection of pepsin," which is herein incorporated by reference. A sensor may be configured to include one or more recognition element, such as one that is immobilized or otherwise embedded in a matrix structure. In some embodiments, a recognition element may specifically bind a substance. In some embodiments, a recognition element may recognize one or more chemical substance. In some embodiments, a recognition element may recognize one or more biological, artificial, or synthetic substance. In some embodiments, a recognition element may recognize one or more microbial factor or contaminant. A recognition element may include at least one cell, protein, nucleic acid, carbohydrate, lipid, conjugate, synthetic molecule, or mimetic. A recognition element may be located within a matrix, for instance conjugated to a matrix of agarose beads, or embedded or encapsulated within a matrix structure. A recognition element might itself be a biological agent, for example: a *staphylococcus* protein A complex, which generally binds immunoglobulins; a binding peptide or protein like an immunoglobulin; a DNA binding protein; a genetically engineered protein; a nucleic acid; an aptamer; a carbohydrate; a lipid; a conjugate; or a synthetic molecule like an artificial antibody or other mimetic. See, for example, U.S. Pat. No. 6,255,461 to Mosbach et al., titled "Artificial antibodies to corticosteroids prepared by molecular imprinting," U.S. Pat. No. 5,804,563 to Still et al., titled "Synthetic receptors, libraries and uses thereof," U.S. Pat. No. 6,797,522 to Still et al. titled "Synthetic receptors," U.S. Pat. No. 5,831,012 to Nilsson et al., titled "Bacterial receptor structures" and US Patent Application No. 2004/0018508 to Friedman, titled "Surrogate antibodies and methods of preparation and use thereof," which are incorporated herein by reference. A recognition element may include an antibody, such as an antibody saturated with a labeled form of the target, as described in U.S. Pat. No. 5,183,740 to Ligler et al., titled "Flow immunosensor method and apparatus," which is herein incorporated by reference. In embodiments where glucose is a substance to be optically detected by the external device, the recognition element of the sensor may be a malachite green acceptor covalently linked to insulin. See, for example, Tolosa et al., "Lifetime-based sensing of glucose using energy transfer with a long lifetime donor," *Analytical Biochemistry* 250: 102-108 (1997), which is herein incorporated by reference.

In certain embodiments, a recognition element 145 might be encapsulated in one or more emulsion or other encapsulating material 140. Encapsulation or emulsion may be utilized instead of or in addition to distribution throughout the sensor and/or in the matrix. Proteins, for instance, have been shown to maintain their function when encapsulated. For more information regarding encapsulation of proteins, see, for example: "Fluorescence detection of enzymatic activity within a liposome based nano-biosensor," Vamvakaki et al., *Biosens Bioelectron.* 21:384-8 (2005); Sotiropoulou, et al., "Stabilization of enzymes in nanoporous materials for biosensor applications," *Biosens Bioelectron* 20:1674-1679 (2005); and Besanger, et al., "Screening of inhibitors using enzymes entrapped in sol-gel-derived materials," *Anal. Chem.* 75, 2382-2391, (2003), which are herein incorporated by reference. Emulsions and encapsulating materials can, for example, include one or more carbohydrate, alginate, protein, protein cage, lipid, phospholipid, liposome, cerasome, oil, emulsion, or a polymer. Encapsulating materials may include photopolymerized water-soluble molecules, such as those described in U.S. Pat. No. 6,258,870 to Hubbell et al., titled "Gels for encapsulation of biological materials," which is herein incorporated by reference.

In some embodiments, the sensor may include one or more biological agent. For example, the sensor may include at least one biosensor. As used herein, "biosensor" refers to a sensor including at least one biological agent or biological component. A biosensor may include biologic agents such as cells, proteins, peptides, nucleic acids, aptamers, lipids, or carbohydrates. A biosensor may include in part a recognition element such as a cell, a protein, a nucleic acid, an aptamer, a lipid, and/or a carbohydrate, configured to transmit a signal when a substance is detected. For example, a matrix may include a biosensor. For example, a recognition element may include one or more genetically engineered cells, which may be configured within solution or immobilized in alginate within the matrix. Such genetically engineered cells may be configured to detect a substance through a receptor and then to produce a bioluminescent signal. See, for example, Daunert et al., "Genetically Engineered Whole-Cell Sensing Systems: Coupling Biological Recognition with Reporter Genes," *Chem. Rev.* 100(7): 2705-2738 (2000), which is herein incorporated by reference. As another example, a recognition element may include an encapsulated enzyme configured to recognize a substance as a substrate wherein the encapsulated enzyme is conjugated or otherwise associated with a responsive fluorescent compound. See, for example, Vamvakaki et al., "Florescence detection of enzymatic activity within a liposome based nano-biosensor," *Biosensors and Bioelectronics* 21: 384-388 (2005), and Sotiropoulou, et al., "Stabilization of enzymes in nanoporous materials for biosensor applications," *Biosensors and Bioelectronics* 20:1674-1679 (2005), and Besanger, et al., "Screening of inhibitors using enzymes entrapped in sol-gel-derived materials," *Anal. Chem.* 75:2382-2391 (2003), which are herein incorporated by reference. As another example, one or more component of a biosensor may be a biologically active molecule bound to a surface, for example using gold-binding fusion proteins. See, for example, the product description from BioHesion™ titled "Advanced Surface Binding Technology," which is herein incorporated by reference. For example, a biosensor may include a bacterial protein. See "Scientists develop biosensor to detect E. Coli bacteria," *RxPG News*, Aug. 19, 2006, which is herein incorporated by reference.

In some embodiments, the sensor may include at least one chemical sensor. A chemical sensor may be configured to detect chemical substances present in beverage fluid, for example contaminants or additives that are not generally considered to be healthful. For example, the sensor may detect a chemical agent, such as a pollutant, allergen or additive. Such a chemical agent may be undesirable or dangerous for consumption by some individual users. A chemical sensor may also be configured to detect chemical substances present in salivary fluid, for example chemicals or metabolites ingested by an individual before that individual drinks from the beverage container. Multiple types of chemical sensors may be implemented. See, for example, Snow et al., "Chemical Detection with a Single-Walled Carbon Nanotube Capacitor," *Science* 307:1942-1945 (2005), which is incorporated herein by reference.

A sensor may be configured to be responsive to a taggant, which may be bound to a substance. A taggant, as used herein, refers to a chemical or physical component which is configured to be detectable, such as through direct visual or olfactory detection by a user, or detection through a device or assay. A taggant is configured to enhance detection of one or more substance, either directly or indirectly. For example, a taggant bound to a substance may be directly detected. For example, a taggant released when a substance binds to a recognition element may be an indirect indicator of the presence of the substance. Numerous types of taggants exist and various configurations may be utilized. A taggant 155 can include a dye, chromogen, a fluorescent substance, a luminescent substance, an odorant, a protein, a nucleic acid like an aptamer, a carbohydrate, a lipid, a synthetic molecule, a quantum dot, an optically active compound, a magnetic compound, a genetically engineered protein, a molecule configured for release, a resonance energy transfer molecule, a metal, a mass-label molecule, a radioisotope, or a volatile compound. For example, see US Patent Application No. 2003/0022225 to Monforte et al., titled "Releasable nonvolatile mass label molecules," U.S. Pat. No. 6,635,452 to Monforte et al. titled "Releasable nonvolatile mass label molecules," U.S. Pat. Nos. 5,516,931, 5,604,104 and 5,602,273 to Giese et al., titled "Release tag compounds producing ketone signal groups," U.S. Pat. No. 5,360,819 to Giese titled "Molecular analytical release tags and their use in chemical analysis," and U.S. Pat. No. 6,491,643 to Katzman and Carlebach, titled "Breath test analyzer," which are herein incorporated by reference. A taggant 155 may be included in a matrix 120 and released when a substance binds, such as in a displacement assay. In some embodiments, a taggant 155 may be included in a matrix structure or retaining materials of a beverage immersate. In some embodiments, a beverage immersate 110 may be configured to store a taggant 155 at a distance from a matrix 120. A taggant storage region may be configured to release a taggant at a specific time or in response to a condition, such as physical pressure, temperature, pH or hydration. For example, a taggant may be released through flexing of a support surface configured to be responsive to binding of a substance to recognition elements. See, for example, Boisen et al., "Rapid molecular detection of food- and water-bourne diseases," *Microbiology Today*, August 2007, 116-118, which is herein incorporated by reference. The taggant 155 may be dehydrated prior to use, including dehydrated in complex with a recognition element 145. See, for example, U.S. Pat. No. 5,354,654 to Ligler et al., titled "Lyophilized ligand-receptor complexes for assays and sensors," which is herein incorporated by reference. The taggant 155 might be a passive label for the substance 125, such as a nonspecific dye like a cyanine dye, configured to bind to nucleic acids. Instead of or in addition, the taggant 155 may be configured to be responsive to binding of the substance 125, for example a labeled recognition element 145 like a fluorescein-conjugated antibody able to complex with the substance 125, or a recognition element 145 like a transferase that is configured to include a recognition site for the substance 125 and is configured to transfer the taggant 155 as a labeled modifier like a phosphate or carbohydrate group. See, for example, US Patent Application No. 2003/0022225 to Monforte et al., titled "Releasable nonvolatile mass label molecules," U.S. Pat. No. 6,635,452 to Monforte et al. titled "Releasable nonvolatile mass label molecules," which are herein incorporated by reference. A taggant may be activatable in the presence of one or more substance. If the substance 125 or the recognition element 145 includes a catalyst or enzyme, the taggant 155 may also include a substrate with a taggant configured to be cleavable or activatable. Another example would include a recognition element 145 configured to exhibit altered conformation upon binding the substance 125, such as a calcium-dependent binding molecule like calmodulin, possibly as part of a fusion protein, and/or configured to allow resonance transfer. See, for example, Miyawaki et al., "Fluorescent indicators for $Ca^{2+}$ based on green fluorescent proteins and calmodulin," *Nature* 388: 882-887 (1997), which is incorporated herein by reference. The taggant 155 might also be incorporated in or intrinsically part of one or more material forming the matrix 120 or the beverage immersate 110, and responsive to binding of the substance 125, such as a stimuli-responsive gel.

In some embodiments, the recognition element 145 may include a releasable taggant compound. For example, a recognition element may be configured to release a taggant in response to the binding of a substance. Many types of releasable compounds are available, such as nonvolatile mass tags. See, for example, US Patent Application No. 2003/0022225 to Monforte et al., titled "Releasable nonvolatile mass label molecules," and U.S. Pat. No. 6,635,452 to Monforte et al. titled "Releasable nonvolatile mass label molecules," which are herein incorporated by reference. Volatile release taggants may also be utilized in some embodiments. See, for example, U.S. Pat. No. 5,610,020 to Giese et al., titled "Release tag compounds producing ketone signal groups," which is incorporated herein by reference. In some embodiments, a releasable taggant 155 may be presented in the matrix 120 as a lipid layer. See, for example, U.S. Pat. No. 6,949,347 to Singh and Chan-Hui, titled "Multiplex analysis using membrane-bound sensitizers," which is herein incorporated by reference.

In some embodiments, the sensor may include a matrix 120 that includes a gel configured to be responsive to a substance, wherein the gel is configured to emit a signal when the substance is detected. A gel configured to emit a signal when the substance is detected may be a signal emitter configured to transmit a signal responsive to the at least one sensor. For example, a signal emitter may be configured to emit an audible signal responsive to the sensor. A signal may include a chromatic, fluorescent, luminescent, or aromatic signal, including as a releasable taggant. In some embodiments a responsive gel may be configured as at least one sensor integral to the beverage immersate 110. For example, a responsive gel may be operably connected to a transducer configured to convert the response of the gel into a signal. The presence of a substance, such as an analyte, may elicit a response from the gel, such as swelling, light emission or release of a taggant, which may be detected by a detector integral to the external device. The beverage immersate 110 may be configured to allow access to the gel through a permeable area of a covering, and/or a selective medium. A responsive gel may include a swellable hydrogel operably connected to a transducer, such as a pressure sensor configured to convert the swelling response of the gel into a signal. See, for example, Bromberg, "Intelligent polyelectrolytes and gels in oral drug delivery," *Current Pharmaceutical Biotechnology* 4: 339-349 (2003), which is herein incorporated by reference. A swellable hydrogel may include proteins such as the reversibly swellable, biodegradable, cation-binding hydrogel described in U.S. Pat. No. 6,310,105 to Damodaran, titled "Carboxyl-modified superabsorbent protein hydrogel," which is herein incorporated by reference. In some embodiments, the swelling response of a gel may have stages responding to various ligands, which may be configured to be detectable by one or more transducers configured to respond to various stages of swelling. See, for example, Ehrick et al., "Genetically engineered protein in hydrogels tailors stimuli-responsive characteristics," *Nature Materials* 4: 298-302 (2005), which is herein incorporated by reference. Examples of a transducer that may be configured for use with a responsive gel include a pressure sensor, with may be fabricated from a piezoelectric material, such as an acoustical wave sensor or a cantilever sensor configured to convert the pressure of the gel into a sound, radiowave or wireless signal. See, for example: Drafts, "Acoustic Wave Technology Sensors," Sensors Magazine Online, Oct. 1, 2000; Tanaka et al., "Polymer gels that can recognize and recover molecules," *Faraday Discuss.*, 102: 201-206 (1996); and Liu and Ji, "Detection of $Pb^{2+}$ using a hydrogel swelling microcantilever sensor," *Analytical Sciences*, 20:9-11 (2004), which are herein incorporated by reference. In some embodiments, a detector in an external device may receive a wireless signal through a port, and process the signal into results for display to at least one system user. The beverage immersate 110 may include a mechanism for removal of the hydrogel, for example by opening the beverage immersate 110 for removal or replacement of a module.

An example of a sensor includes a polymerized crystalline colloidal array responsive to a substance. For example, a sensor may be fabricated to include a crystalline colloid array comprised of charged polystyrene spheres that are polymerized within a hydrogel that swells or shrinks in response to a substance (e.g. see Holtz and Asher, "Polymerized colloidal crystal hydrogel films as intelligent chemical sensing materials," *Nature* 389: 829-832 (1997) which is herein incorporated by reference). See, for example, U.S. Pat. Nos. 6,187,599 and 6,544,800 to Asher et al., titled "Polymerized crystalline collidal arrays," and U.S. Pat. No. 7,105,352 to Asher titled "Intelligent polymerized crystalline colloidal array carbohydrate sensors," which are herein incorporated by reference. The Asher group at the University of Pittsburgh has also described the fabrication of polymerized crystalline colloidal arrays. See the attached printout of the Asher Laboratory materials titled "Colloid Group," accessed online at the Asher Laboratory website on Mar. 9, 2009, which are incorporated herein by reference. Crystalline colloidal arrays diffract light at (visible) wavelengths determined by their lattice spacing, which gives rise to intense colors. Swelling of the hydrogel including the polymerized crystalline colloid array changes the lattice spacing and causes a shift in the Bragg peak of diffracted light to longer wavelengths. The crystalline colloidal array further includes a recognition element, such as an antibody, which specifically recognizes and binds a substance (see, e.g., Holtz and Asher, "Polymerized colloidal crystal hydrogel films as intelligent chemical sensing materials," *Nature* 389: 829-832 (1997) and U.S. Pat. No. 6,753,191 to Asher and Reese, titled "Polymerized crystalline colloidal array chemical sensing materials for use in high ionic strength solutions" and U.S. Pat. No. 6,214,546 to Asher et al., titled "Detection of biomolecules," which are herein incorporated by reference). The beverage immersate may be configured so that a color change in the crystalline colloid array of the sensor is visible to an individual user. To measure the peak diffraction wavelength, the beverage immersate including the sensor is screened with a spectrometer associated with a detection device. For example, the detection device includes an integrated spectral sensing system having an energy (light) source and a detector (see e.g. U.S. Patent Application 2008/0265146 to Coates, titled "Integrated sensing module for handheld spectral measurements," and U.S. Pat. No. 7,459,713, to Coates, titled "Sensing system approach for handheld spectral measurements having a disposable sample handling apparatus," which are herein incorporated by reference). The shift in peak diffraction wavelength may be correlated with substance concentration (see Holtz et al, Ibid.), and the results processed by circuitry in the detection device. Results may recorded as digital memory in the detection device, an associated network, and/or an additional device (such as a laptop or PDA). Results may be communicated to a system user, such as through an indicator on a user interface integral to the detection device.

In some embodiments, a beverage immersate 110 may also include microcircuitry 115. Microcircuitry may include one or more signal transmitter, such as an antenna, vibration emitter, light source (e.g. LED light) or RF signal emitter. A signal emitter comprising microcircuitry may be configured to transmit a signal responsive to the at least one sensor. Microcircuitry may include one or more memory element. In some embodiments, a beverage immersate 110 may include a power source 150, for example one or more batteries, electrical connections with an external power source or one or more power-generating elements such as solar cells. The beverage immersate 110 may include one or more power sources such as, for example, a battery, microbattery, solar energy converter, fuel cell, biofuel cell, or power cord. In some embodiments, wireless transmission may serve as a means to power the system, including the beverage immersate 110. See US Patent Application No. 2005/0143787 to Boveja titled "Method and system for providing electrical pulses for neuromodulation of vagus nerve(s), using rechargeable implanted pulse generator," which is herein incorporated by reference. One or more power sources may be rechargeable or replaceable.

FIG. 2 illustrates aspects of a beverage immersate 110. As shown in FIG. 2, in some embodiments a beverage immersate 110 includes a selectively permeable area 200 configured to allow at least one substance from fluid to enter or permeate into at least one region of the beverage immersate 110 such as an internal cavity 212. For purposes of illustration, a selectively permeable area 200 is shown as a single relatively small area, but depending on the embodiment, one or more selectively permeable areas could be of any size and distribution, including distributed across the entire or a substantial portion of the surface of the beverage immersate. The selectively permeable area 200 could include a covering, which might be a screen, possibly including a porous version of the same material as the outer wall 220 of the beverage immersate. The selectively permeable area 200 could include a selective medium of a type configured to filter out, for example, debris, cells, molecules of a range of sizes, charged molecules or any other undesirable material, including excess moisture, while being configured to allow some other substances to pass through. Such a selective medium could be fabricated from any of a number of materials including charcoal or cellulose; a synthetic polymer such as but not limited to polyethylene, polycarbonate, nylon, polyester, polysiloxane, or polypropylene; a hydrogel, or a monolayer or bilayer of lipids; a selective medium could include a protein. Selective medium may include at least one of charcoal, cellulose, synthetic polymer, polyethylene, polycarbonate, nylon, polyester, polypropylene, polysiloxane, gel, hydrogel, lipid, and protein. For example, the selective medium could be one made of cellulose configured with pores sized to allow diffusion of certain sized molecules, a hydrogel film of a type that swells at a certain pH, a gas-permeable membrane or a hydrophobic lipid bilayer. See, for example, "A hydrogel-based CO2 sensor," Herber and Olthuis, MESA+Institute for Nanotechnology, University of Twente, which is incorporated herein by reference. For example, a selective medium may include biocompatible membranes such as those described in U.S. Pat. No. 6,258,870 to Hubbell et al., titled "Gels for encapsulation of biological materials," which is herein incorporated by reference. A selective medium could also or instead include one or more active transporter, such as a porin or ion transporter.

As illustrated in FIG. 2A, a beverage immersate 110 may include at least one internal cavity 212 containing one or more modular units 215. Modular units 215 may be configured to be replaceable, swappable, rechargeable, or removable. For example, modular units may be configured to be removed for analysis by an external detection device. For example, modular units may be configured to be removable and exchanged or swapped with other modular units. For example, modular units may be configured for removal and replacement. In some embodiments, an internal cavity 212 may be configured to contain more than one modular unit at a time. Access to an internal cavity may be made, for example, through a lid region 205 configured to cover one or more sides or external portions of the beverage immersate 110. A lid region 205 may be configured to open and close through a hinge 210 or other mechanism as suitable to an embodiment. A lid region 205 should preferably be configured to seal or close securely, such as to prevent the lid region from opening during use or transport, or to prevent leakage around the lid region opening.

One or more modular units 215 of the beverage immersate 110 may be configured to passively collect beverage fluids and/or constituents thereof, including cells or other biologics, in an internal cavity 212. In some embodiments, the beverage immersate 110 may include a passive sampling container, and one or more gel or gel-like materials may include an absorbent made from one or more material like those mentioned herein, which may be dehydrated in its initial state prior to contact with beverage fluid. A beverage immersate 110 may include at least one material from the list including absorbent, adsorbent, proteoglycan, charged polymer, polylysine, silica gel, alumina gel, and ion exchange resin. An internal cavity 212 may include, possibly as a coating on the surface of the internal cavity 212, a synthetic or natural adsorbent material of a type that promotes the adhesion of one or more constituent in the beverage fluid, like a cell or a protein. A beverage immersate 110 may include at least one of a carbohydrate, alginate, protein, protein cage, lipid, phospholipid, liposome, cerasome, oil, emulsion, polymer, spheres, microspheres, or nanospheres. See US Patent Applications Nos. 2004/0115132, 2006/0204444 and 2007/0059245 to Young et al., titled "Protein cages for the delivery of medical imaging and therapeutic agents," and US Patent Application No. 2006/0292174 to de los Rios and Oh titled "Self-assembling nanoparticle drug delivery system," which are herein incorporated by reference. A beverage immersate 110 may include a hydrogel including hybrid materials, for example a hydrogel containing a hybrid protein-polysaccharide material. See U.S. Pat. No. 6,821,331 to Damodaran, titled "Protein-polysaccharide hybrid hydrogels," which is herein incorporated by reference. For example, a beverage immersate may include a proteoglycan or a charged polymer such as polylysine. Other retaining materials may be included, such as semi-specific or non-specific adsorbents, such a silica ($SiO_2$) or alumina ($Al_2O_3$)— containing gel or an ion exchange resin, including as part of a matrix.

A beverage immersate 110 may include at least one electronic chip sensor, which may be configured as a modular unit. An electronic chip sensor may be configured for reuse, multiple use, or single use. An electronic chip sensor may be removable, swappable, or replaceable, such as an electronic chip sensor configured as a module. An electronic chip sensor may be configured to interface directly with an external device through a port configured for communication, such as a port configured for communication through electronic circuitry. An electronic chip sensor may be configured to interface directly with an external device through a port configured for communication, such as a port configured for communication through one or more wavelengths of light. An electronic chip sensor may be configured to interface directly with an external device through a port configured for communication, such as a port configured for communication through vibration. In some embodiments, the interface between an electronic chip sensor and an external device may be enhanced through a surface component of the beverage immersate 110. For example, a surface component of the beverage immersate may be configured to amplify or transmit one or more wavelengths of light. For example, a surface component of the beverage immersate may be configured to amplify or transmit vibration. Other instrumentation associated with the beverage immersate 110 may interact with the electronic chip sensor, such as one or more microfluidic device, which may be integrated into an external device. Examples of electronic chips that may be configured for use with some embodiments includes immunoassay microchips and electrochemical DNA sensor chips. See, for example, Dill et al., "Immunoassays and sequence-specific DNA detection on a microchip using enzyme amplified electrochemical detection," *J. Biochem. Biophys. Methods* 5: 181-187 (2004) and Drummond et al., "Electrochemical DNA sensors," *Nature Biotech.* 21: 1192-1199 (2003), which are incorporated herein by reference. An electronic chip sensor may be configured for use with electronic, acoustic, or wireless technology to communicate remotely with an external device through a port, such as when a port is configured to be a receiver. See, for example: Yazawa et al., "A wireless biosensing chip for DNA detection," *ISCC* 2005 30.6; Baker, "Beaming Biodata," *MIT Technology Review* May 2005 (on-line edition); Heim, "Lab on a swab," *MIT Technology Review*, Aug. 29, 2005; and Hitachi Ltd. News Release "Development of the world's first RFID sensor chip for DNA analysis—SNPs in DNA detected using chip and reader only," Feb. 10, 2005, which are incorporated herein by reference. In some embodiments, a beverage immersate 110 including one or more electronic chip sensor may include a power source, which may be configured to supply power to an electronic chip sensor through an electric transmission element, such as wires. A power source for a beverage immersate 110 may include one or more rechargeable elements. A power source for a beverage immersate 110 may include one or more transmitted power sources. See US Patent Application No. 2005/0143787 to Boveja titled "Method and system for providing electrical pulses for neuromodulation of vagus nerve(s), using rechargeable implanted pulse generator," which is herein incorporated by reference.

FIG. 2B illustrates, in cross section, some components that, depending on the embodiment, may be located internally to a beverage immersate 110. A beverage immersate 110 may include an inner wall 225 configured to enclose one or more components of the beverage immersate 110 configured to be operable in contact with fluid, and an outer wall 220. As shown in FIGS. 2A and 2B, the inner wall 225 may be configured to form one or more internal cavity 212. FIG. 2B illustrates a selectively permeable area 200 configured to allow a substance 125 access to a matrix 120 within an internal cavity 212 of the beverage immersate 110. An inner cavity 212 may include a sensor, such as a sensor including a matrix 120 including a recognition element 145. A matrix 120 may be configured as a modular unit 215. The matrix 120 may include one or more recognition element 145, including an encapsulated recognition element 140. A recognition element 145 is configured to specifically recognize and retain the substance 125, as illustrated 130. A matrix 120 may include one or more taggant 155. An inner cavity 212 may also include a transducer 265, configured as a signal transmitter, for example a transducer operably coupled to the matrix 120 and configured to detect binding of a substance 125 to a recognition element 145 within the matrix 120. An inner cavity 212 may also include microcircuitry 115. An inner cavity 212 may also include one or more sensing element 230. One or more sensing element 230 may include, for example, a pH sensor, a temperature sensor, a time sensor, or a pressure sensor. A time sensor may include a sensor of elapsed time, such as duration of time from an event such as when the beverage immersate came into contact with a fluid, or when the beverage immersate lid 205 was closed, or a similar beverage immersate activation event. A transducer 265 and sensing element 230 may be connected to microcircuitry 115. A transducer may be configured to convert information from the sensor into a wireless signal that is transmissible to a detection device. For example a responsive gel may be operably connected to a transducer configured to emit a RF signal in response to a substance binding the responsive gel. A transducer may be operably connected to the transmitter via micorcircuitry.

As depicted in FIG. 2B, an enclosed region 270 may be configured between an outer wall 220 of the beverage immersate 110 and an inner wall 225. An outer wall 220 and an inner wall 225 of a beverage immersate 110 may be configured to include an enclosed region 270 within the space between the outer wall 220 and inner wall 225. An enclosed region 270 may include components that are operable without being in contact with a fluid. For example, an enclosed region may include one or more microprocessor 250, one or more controllable switch 245, one or more battery 255, and one or more antenna 260. An enclosed region 270 may also include at least one signal emitter, for example one or more light emitter 235 and one or more vibration emitter 240. An enclosed region 270 may be configured to protect regions or components of the beverage immersate 110 from extreme temperatures, salts or other components of a beverage, or beverage fluid. An enclosed region may include material of a density configured to alter the density of the beverage immersate relative to a beverage fluid, for example an air or gas pocket, or a material denser than water. An enclosed region 270 may contain components which are operably connected to an inner cavity 212, such as a controllable switch 245, microprocessor 250, battery 255, light emitter 235, or vibration emitter 240, which may be operably connected to components within an internal cavity 212 through a wire or wireless connection.

A signal generated by a signal transmitter integral to a beverage immersate may be, for example, an electrical, visual, magnetic, acoustic, vibrational, heat, light (including infrared (IR) or ultraviolet (UV)), radio frequency (RF) or electromagnetic radiation signal. For example, a system may be configured so that a light emitter is switched on when a substance is recognized by the sensor. For example, a system may be configured so that a vibration emitter creates vibrations which generate sound waves audible or inaudible to human hearing when a substance is detected. For example, a system may be configured so that a vibration emitter generates vibrations which generate wave action in a beverage container with wave length and wave height sufficient for visible detection. Such wave length and wave height would of course vary depending on factors such as the size, shape, fluid depth of the beverage container and relative location of an individual or detection device observing the waves. For example, a system may be configured so that a vibration emitter generates vibrations that are detectable to a detection device, for example a mechanical wave detector.

The beverage immersate may include at least one signaling element. A signaling element may function to emit a signal after contact between the beverage immersate and fluid has occurred, for example to signal a system user that the system is operating. Depending on the embodiment, a system including a signaling element may be configured to signal contact with fluid at a specific point. Depending on the embodiment, a system including a signaling element may be configured to signal lack of contact with fluid, or insufficient contact, at a specific point. For example, a system including a signaling element may be configured to signal contact with fluid relative to at least one of time, presence of a target material, or presence of amount of a target material. A target material may include, for example, the substance detected by the sensor, or a reference or additional substance. For example, the target material may be water, and the signaling element may be configured to indicate that a fluid containing water has been detected. As beverages would be expected to contain some portion of water, a system including such a signaling element may function to indicate to a system user that the system has sufficient contact with a beverage fluid for relevant function. For example, the target material may be ethanol, and the signaling element may be configured to indicate that a fluid containing ethanol (i.e. an alcoholic beverage) has been detected. As alcoholic beverages would be expected to contain some portion of ethanol, a system including such a signaling element may function to indicate to a system user that the system has sufficient contact with an alcoholic beverage fluid for relevant function. A system including such a signaling element may also confirm that the beverage is an alcoholic beverage and not a nonalcoholic version or similar-appearing beverage. For example, a system may include a signaling element and a timekeeping device operably attached to a fluid sensor and a signal emitter, configured so that a user would be alerted that fluid had or had not been detected during a preset period of time. For example, a system may include a signaling element operably attached to a sensor so that the sensor will cause a signal to be generated when a substance is present or absent after a particular period of time. For example, a system may include a signaling element operably attached to a sensor so that the sensor will cause a signal to be generated when the sensor has detected a quantity of the substance after a particular period of time. For example, the signaling element may be configured to emit a signal when more than a threshold level of water has been detected in a fluid. Signaling elements may include, for example, electronic elements such as an acoustic wave generator, a vibration emitter or an electric light. For example, a signal emitter may beep, vibrate or flash light after the beverage immersate has been in contact with fluid for a preset period of time and therefore indicate to a user that the beverage immersate system is operational. Signaling elements may include, for example, electronic elements such as a small electric shock emitter, or a transmitter to send data to an external device, such as a detection device. The detection device may be configured to include a signaling element, for example by displaying text on a display such as "system operational" or by illuminating a specific indicator in a user interface. Signaling elements may include chemical elements such as chemical dyes, inks, chromogens, or fluorogens. For example, a beverage immersate may be configured with a color indicator that changes color in the presence of a target material. See, for example, US Patent Application No. 2002/0044891 to Miller et al., titled "Food Quality Indicator Device," which is herein incorporated by reference. Signaling elements may include flavorants, such as a signaling element configured to emit a flavorant with an unpleasant flavor after a threshold quantity of a substance has been detected. Such a system may indicate to an individual beverage consumer that a beverage contains, for example, a greater than desirable concentration of a target material such as ethanol, glucose, fructose, saccharin, pollutant, allergen, irritant, or other substance.

The beverage immersate may include at least one flavorant or flavoring agent such as those common to the food industry. For example, the beverage immersate may include at least one flavorant incorporating flavoring agents and a carbohydrate, gelatin or oil based compound. A flavorant may be a natural flavorant, such as the essential oil, oleoresin, essence or extractive, protein hydrolysate, distillate, or any product of roasting, heating or enzymolysis, which contains the flavoring constituents derived from a spice, fruit or fruit juice, vegetable or vegetable juice, edible yeast, herb, bark, bud, root, leaf or any other edible portions of a plant, meat, seafood, poultry, eggs, dairy products, or fermentation products thereof, whose primary function in food is flavoring rather than nutritional. A flavorant may include one or more salts, sugars, artificial sweeteners, or flavor enhancers. For example, the beverage immersate may be covered with a flavorant or flavoring agent. For example, the at least one flavorant or flavoring agent may be a carbohydrate, gelatin or oil based coating on the surface of the beverage immersate. For example, the at least one flavorant or flavoring agent may be coated, dried or glazed onto the exterior of the beverage immersate. For example, at least one flavorant may be encapsulated or included in an emulsion integral to a beverage immersate. In some embodiments, the flavorant may be initially located in an indentation, reservoir or internal region of the beverage immersate that is configured to release the flavorant in response to a condition, such as a temperature or pH. In some embodiments, the flavorant may be initially located in an indentation, reservoir or internal region of the beverage immersate that is configured to release the flavorant in response to a sensor. In some embodiments, the at least one flavorant is of a type expected to influence an individual, for example being configured to emit an unpleasant flavor in response to a sensor result or to a received signal from an external device or network. In some embodiments, a flavorant may encourage at least one individual to drink the beverage fluid in which the beverage immersate is immersed. For example, a flavorant that tastes like candy, such as a bubble gum or cotton candy flavor, may be desirable for use with children. For example, a flavorant tasting like mint or spice flavor may be desirable for use with adults. For example, a flavorant tasting like meat, such as chicken or beef flavor, may be desirable for use with cats or dogs. In some embodiments, the at least one flavorant is configured to change chemical composition during contact with fluid relative to at least one of time, presence of a target material, or presence of an amount of a target material. For example, a flavorant may be configured with a limited quantity of flavoring agent and therefore configured to lose flavor after a finite length of time. For example, a flavorant may be configured with a limited quantity of a dissolvable flavoring agent, such as a sugary compound configured to dissolve after contact with a particular amount of fluid. For example, the flavorant may bind to a target material in fluid, thereby reducing the levels of unbound flavorant available for tasting and reducing the length of time that an individual may taste the flavorant. For example, a flavorant may be encapsulated or emulsified with a carbohydrate substrate which is configured to dissolve after contact with sufficient fluid. See, for example, U.S. Pat. No. 6,746,529 to Witteveen et al., titled "Stable, spray-dried composition in a carbohydrate substrate and process for obtaining said composition," which is herein incorporated by reference. Flavorant release may be operably connected to a sensor so that flavorant is released when a substance is detected, or not detected over a period of time. For example, if insufficient mucin is detected over time, a salivary-fluid enhancing flavorant may be released. In some embodiments, the flavorant may be targeted to one or more group of users, for example a flavorant with sour flavor may be desirable to encourage a sufficient quantity of salivary fluid in the oral cavity in individuals with characteristically dry mouths. Citric acid, for example, has been shown to stimulate salivary fluid expression or production. See U.S. Pat. No. 6,102,872 to Doneen et al., titled "Glucose detector and method," which is herein incorporated by reference.

A beverage immersate may contain at least one reservoir. For example, a beverage immersate 110 may include at least one reservoir within an internal cavity 212. For example, a beverage immersate may contain at least one reservoir in an enclosed region 270 configured between an outer wall 220 of the beverage immersate 110 and an inner wall 225. A reservoir may be configured to passively release at least one agent, for example to passively diffuse an agent into a fluid over time. A reservoir may be configured to actively release at least one agent, for example with a valve or aperture that is actively controlled by a controllable switch operably connected to a microprocessor. An active release may be initiated by the system based on preset criteria, for example, at a preset time, or after a preset amount or concentration of a substance has been detected. An active release may be initiated in response to a signal, such as a signal from a transducer or received from an antenna. An active release may be initiated by a system user, such as through an external device or network. A reservoir may be configured to release a medicinal agent. A medicinal agent may include at least one expectorant, bronchodilator, cough suppressant, vasodilator, analgesic, antiseptic, anti-infective, antibiotic, antihistamine, anti-leukotriene, anti-cholinergic, nutritional supplement, therapeutic, enzymatic substrate, diagnostic challenge, methacholine, sensitizer, or taggant. A reservoir may be configured to release a flavorant. A reservoir may be configured to release a color indicator, such as a material that changes the color of the beverage immersate. A reservoir may be configured to release a color indicator, such as a material that is released into the fluid and changes the color of the fluid. A reservoir may be configured to release an antidote or neutralizer in response to a specific substance being detected. For example, a system may include a reservoir configured to release an antimicrobial agent in response to a microbial agent binding to a sensor. For example, a reservoir may be configured to release a specific microbial cell-surface binding agent, such as laminin, in response to a specific microbe being detected, such as *E. Coli*.

The beverage immersate or a portion thereof could be of a single or multiple use type. For example, the beverage immersate may include modular units that may be replaced or recharged after use while other modular units may be durable and configured for multiple instances of use. For example, as illustrated in FIG. 2, a beverage immersate 110 may include an outer wall 220 made from a durable plastic, metal, or fibrous material that is configured for use multiple times, while one or more internal modules may be replaced as they become spent, full, or to alter the modality of the beverage immersate 110. For example, modules including different types of recognition elements may be switched into or out of the beverage immersate for particular applications. For example, modules including one or more colorant or dye may be switched in and out, such as to replace a spent or depleted module or to replace a module of a color or dye with one containing a different color or dye. For example, modules containing one or more recognition element may be exchanged, such as when the beverage immersate is configured by a user for detection of a different substance. Modules may be configured for exchange as needed for detection of a different analyte. For example, a modular sensor with certain detection capabilities may be replaced with a modular sensor having the same or other detection capabilities. For example, a modular matrix containing a particular recognition element may be replaced with a new modular matrix containing the same recognition element or a different recognition element.

The beverage immersate may be configured as a single unit with a plurality of regions, units, or modules, and may include layers of material. For example, a beverage immersate may include layers of supporting materials or gels. For example, a beverage immersate may include matrix or shell structures. FIG. 3 depicts various aspects of potential material configurations within the beverage immersate. For example, as illustrated in FIG. 3A, a beverage immersate may include modules configured in sections 300. Such modules may be configured for enclosure in an internal cavity as shown in FIG. 2. For example, as illustrated in FIG. 3B, a beverage immersate may include layers such as stratified layers 310, and may include one or more units configured as a scaffold. Multiple modular regions or layers may also form an indicator system for presence of a substance, such as described in the PCT patent application publication No. WO 2008/006152 A1 to Brockwell and Holland, titled "Indicator system for determining analyte concentration," which is herein incorporated by reference. In some embodiments, one or more recognition elements 145, 320, 305 may be configured in a region of a beverage immersate. In some embodiments, one or more recognition elements 145, 320, 305 may be configured in a region of beverage immersate, such as within one or more stratified layer 310. In some embodiments, one or more recognition elements 145, 320, 305 may be configured in a region of a beverage immersate, such as within one or more sections or modules 300. In some embodiments, various regions of a beverage immersate may be configured from different materials, such as a different type of gel, like sol gels with varying pore size, or pH-responsive or ion-responsive gels. Embodiments with various regions configured from different materials would allow for the sensing of a variety of substances in different sections of the beverage immersate. Embodiments with various regions configured from different materials would allow for ready identification of sensed analytes, such as by identification that module X senses analyte Y, and therefore if module X has sensed a substance, it is inferred to be analyte Y. This type of configuration is illustrated in FIG. 3A as distinct recognition elements 145 and 320 and in FIG. 3B as additional distinct recognition element 305. Referring now to FIG. 3B, in some embodiments, one or more gel or gel-like materials configured as part of the beverage immersate may include at least one recognition element 305 configured as one or more molecularly imprinted recognition site. See, for example, Byrne et al., "Molecular imprinting within hydrogels," *Advanced Drug Delivery Reviews* 54: 149-161 (2002), Peppas and Huang, "Polymers and gels and molecular recognition agents," *Pharm Res.* 19(5):578-87 (2002), and US Patent Application No. 2007/0190084 to Hilt et al., titled "Polymer network compositions and associated methods," which are herein incorporated by reference. In some embodiments, there may be a plurality of molecularly imprinted recognition sites associated with various recognition elements specific to particular regions of the beverage immersate. In some embodiments, a beverage immersate may include one or more gel configured to recognize and respond to a substance 125, for example a hydrogel that selectively recognizes and sequesters a metal. See, for example, Peppas and Huang, Ibid and Tanaka et al., "Polymer gels that can recognize and recover molecules," *Faraday Discuss.*, 102: 201-206 (1996), which are herein incorporated by reference. Other compounds could similarly be included in the beverage immersate configured in one or more sections or modules 300, or one or more stratified layers 310. For example, regions of the beverage immersate may be configured to include one or more taggant 155. For example, materials may be included in the beverage immersate configured within an emulsion, in a coating, or may be incorporated into a structure such as a gel. In some embodiments, materials may be encapsulated 140, for example configured for release over time or configured for responsive release.

Figure 4:
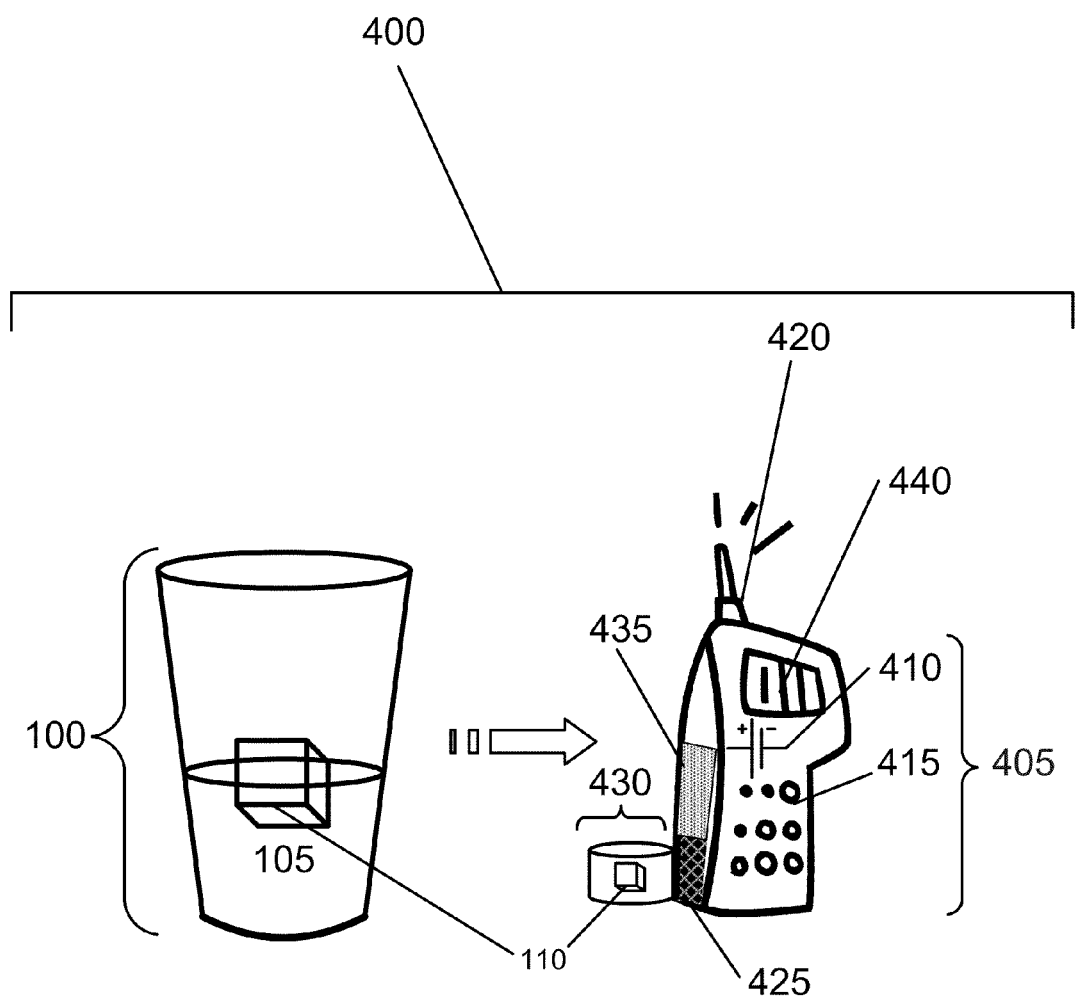
FIG. 4 is a schematic of some aspects of a beverage immersate system.

As illustrated in FIG. 4, in some embodiments a system includes a beverage immersate 110 configured for immersion in a beverage fluid 105 within a personal-use drinking vessel 100. The system includes at least one beverage immersate 110 including at least one sensor configured to detect one or more substance in fluid 105 within a personal use beverage container 100, and at least one external device 405 including at least one port 430 configured to communicate with the at least one beverage immersate 110. The external device 405 may include a detector 425 configured to be able to recognize a signal from the beverage immersate through a port 430, for instance a glass window, a receiver, or a gas port. A sensor may include a gas or chemical sensor, or an optical, acoustic, or electric sensor. A sensor may be an electrochemical sensor. A sensor may be a biological sensor.

An external device 405 is configured to communicate with the beverage immersate 110, for example through detection of signals, such as light, vibration, or transmitted signals from the beverage immersate 110. An external device 405 is configured to communicate with the beverage immersate 110, for example through receiving signals from the beverage immersate. An external device 405 is configured to communicate with the beverage immersate 110, for example through transmission and detection of signals between the detection device and the beverage immersate. An external device 405 is configured to detect at least one signal from the beverage immersate 110, for example a signal from at least one sensor. An external device 405 is configured to detect at least one signal from the beverage immersate 110, such as a signal from an antenna or transmitter integral to the beverage immersate 110. A signal may include, for example, light, sound, vibration, IR, radio, wireless or other detectable signals. A port for communication 430 is operably attached to one or more detectors 425 configured to detect a signal from the beverage immersate, including from a sensor integral to the beverage immersate. For example, where the sensor is configured to emit light after binding one or more substance, the external device 405 may include a light detector, such as a light detector configured to detect non-visible light or light of a specific wavelength. In this example, a port 430 would be configured to allow light from the sensor integral to the beverage immersate to reach a light detector. An external device 405 may be physically connected to the port 430 as illustrated in FIG. 4, or operably connected to the port as suitable for a particular embodiment. For example, in embodiments where the beverage immersate 110 emits light when a substance is present, a detector 425 is operably connected to a port 430 configured to allow the relevant light wavelength to travel to the detector 425. For example, in embodiments where the beverage immersate 110 emits vibration when a substance is present, a detector 425 is operably connected to a port 430 configured to allow the vibration wavelength to travel to the detector 425.

Depending on the embodiment, various possible types of sensors and detector combinations may be utilized within the beverage immersate and the external device 405. Multiple types of sensors are described herein as exemplary types, and others are known in the art. One or more sensor may include, for example, at least one optical sensor, acoustic sensor, electromagnetic sensor, magnetic sensor, electrophoretic sensor, electrochemical sensor, biochemical sensor, microfluidic sensor, magnetic resonance sensor, piezoelectric sensor, surface plasmon resonance sensor, optical microsensor array, surface enhanced raman spectrometer (SERS), laser, ion flow tube, metal oxide sensor (MOS), infrared spectrophotometer, acoustic wave sensor, colorimetric tube, conductive-polymer gas sensor, chemoresistor, selective resonance sensor, gas chromatograph, mass spectrophotometer, or magnetic resonance sensor. As an example of a hand-held tandem mass spectrophotometer that may be integrated into an external device 405, see Gao et al., "Design and characterization of a multisource hand-held tandem mass spectrophotometer," *Anal. Chem.* 80: 7198-7205 (2008), which is herein incorporated by reference. As an example of a gamma-beta radiation detector, see the Ion Ferret™ device available from Overhoff Technology Corporation (Milford Ohio), the 2009 brochure for which is herein incorporated by reference. As an example of a liquid scintillation counter detector, see the Innovative Technology Summary Report titled "Lumi-scint Liquid Scintillation Counter," OST/TMS ID 2311, July 2001, which is herein incorporated by reference. As an example of a visible light, UV or IR detector, see the MiScope® Handheld Digital Microscope, available from Forensics Source (Jacksonville Fla.). As an example of a carbon dioxide or carbon monoxide detector and thermometer, see the AQ2000 hand-held analyzer available from KIMO (France). A sensor and detector may communicate optically and, rely on frustrated total internal detection (FTIR) of magnetic particles, see Gelfand, "Device Offers a Roadside Dope Test," MIT Technology Review Online Edition Aug. 4, 2009, which is herein incorporated by reference.

An external device 405 may be configured to detect at least one signal from at least one beverage immersate 110. An external device 405 may be configured to send at least one signal to at least one beverage immersate 110. A signal may include, for example, light, color changes, sound, vibration, infrared (IR), radio, wireless or other detectable signals. A signal from an external device 405 may be part of the communication between a beverage immersate 110 and the external device 405. For example, an external device 405 and beverage immersate 110 may be integrated with a system to provide light signals such as described in International Patent Application No. WO 99/31560 to Mueller et al., titled "Digitally controlled illumination methods and systems" which is herein incorporated by reference. A signal from at least one sensor integral to the beverage immersate 110 may be part of the communication between the beverage immersate 110 and the external device 405. For example, where the sensor is configured to emit light after binding one or more substance, an external device 405 may include a light detection device, such as a detection device configured to detect non-visible light or light of a specific wavelength. See, for example, US Patent Application No. 2003/0143580 to Straus, titled "Rapid and sensitive detection of molecules," which is herein incorporated by reference. In embodiments in which the beverage immersate 110 and/or an associated taggant is configured to emit optically-detectable signals, the port 430 may include in part or whole an optically-permeable section (e.g. a window), and the sensor or detector may include at least in part a spectrophotometer and/or light source configured to elicit signals from the beverage immersate 110 or taggant. For example, the beverage immersate 110 or taggant may include at least one of a chromogen, fluorescent agent, luminescent agent, a quantum dot, or a compound configured to exhibit alterable optical density. A light source associated with a beverage immersate 110 may include, for example, a light emitting diode or a white light source, such as a source configured to provide light in a variable and/or specific wavelength, including infrared (IR) or ultraviolet (UV). See, for example, U.S. Pat. No. 5,183,740 to Ligler et al., titled "Flow immunosensor method and apparatus," U.S. Pat. No. 7,459,713 to Coates, titled "Integrated handheld sensing system approach for handheld spectral measurements having a disposable sample handling apparatus," US Patent Application No. 2008/0265146 to Coates, titled "Integrated sensing module for handheld spectral measurements," and WIPO Patent Application Publication No. 2007/113727 to Kolesny-Chenko et al., titled "A portable food and/or beverage analyzer and a method of analyzing a food and/or beverage in the field," which are herein incorporated by reference. For example, a light source may be configured to be a part of the detection of the opacity or colorimetric response of a component of the beverage immersate 110. See, for example: U.S. Pat. No. 6,623,698 to Kuo, titled "Saliva-monitoring biosensor head toothbrush;" U.S. Pat. No. 7,314,453 to Kuo, titled "Handheld diagnostic device with renewable biosensor;" US Patent Application No. 2003/0023189 to Kuo, titled "Handheld diagnostic device with renewable biosensor;" and US Patent Application No. 2002/0127143 to Kuo, titled "Saliva-monitoring biosensor electrical toothbrush," which are herein incorporated by reference. In some embodiments, the external device 405 may use electric pulses to measure the conductivity of a beverage immersate 110 component. See, for example, U.S. Pat. Nos. 6,623,698 and 7,314,453 to Kuo, as above. In embodiments in which a taggant is a volatile compound or the substance is in gaseous form, for example an oral or respiratory gas part of the salivary fluid, the beverage immersate 110 may include a gas sensor such as an acoustic wave, chemiresistant, or piezoelectric sensor, such as those described as part of an "electronic nose." See, for example, U.S. Pat. No. 5,571,401 to Lewis et al., titled "Sensor arrays for detecting analytes in fluids," and US Patent Application No. 2004/0006257 to Burch, titled "Detection, diagnosis, and monitoring of a medical condition or disease with artificial olfactometry," which are herein incorporated by reference.

The external device 405 may include at least one communication device including a telecommunication device, a display screen, a speaker, or a printer, which may be operably attached to a data processor. For example, the external device 405 may include at least one reporting device 440. The external device 405 may include at least one reporting device 440, for example visual display elements configured to indicate when a substance has been detected. The external device 405 may include digital memory. For example, the external device 405 may include digital memory that is configured to record received or sent signals, information regarding detected substances, time, temperature or pH associated with the detection, or other data. For example, the external device 405 may include digital memory that is configured to include a medical history of an individual user. For example, the external device 405 may include digital memory that is configured to include medical instructions, such as instructions to display certain medical advice in the event one or more toxic substances are detected. The external device 405 may also include a user interface such as a display screen, touchpad, E-ink device, auditory signal generator, or other interface, for example a keyboard interface 415. The external device 405 may include one or more power source 410, for example one or more batteries, electrical connections with an external power source or one or more power-generating elements such as solar cells. The external device 405 may include one or more power source 410 such as a battery, microbattery, solar energy converter, fuel cell, biofuel cell, or power cord. In some embodiments, wireless transmission may serve as a means to power the system, including the external device 405. See US Patent Application No. 2005/0143787 to Boveja titled "Method and system for providing electrical pulses for neuromodulation of vagus nerve(s), using rechargeable implanted pulse generator," which is herein incorporated by reference. One or more power sources may be rechargeable or replaceable. One or more power source 410 may be operably connected to any module of the external device 405, for example display elements, reporting elements, or communication elements. The external device 405 may include a telecommunication device, which may include an antenna 420 or a cable to transmit and receive information from a network or external computer device, such as a healthcare system computing device or an individual user's cell phone or personal data organizer (PDA). See, for example: US Patent Application No. 2004/0078219 to Kaylor et al., titled "Healthcare networks with biosensors;" US Patent Application No. 2004/0100376 to Lye et al., titled "Healthcare monitoring system;" and Lempert, "Digital house calls? Check your health at home," MSNBC Feb. 21, 2006; which are herein incorporated by reference. The external device 405 may also include additional elements or instrumentation 435 as appropriate to a specific embodiment.

The external device 405 may be configured to communicate with at least one network. A network may be a medical network, such as one that includes at least one medical history, for example a medical history of an individual user, or of a reference individual or group. The medical history may include, for example, genetic or genomic information, drug use history, allergies, medical diagnoses, or surgical history. A network may be a public health response network. For example, a external device 405 may send and receive information from a local health department, such as to report a contaminant or to obtain up to date information regarding possible contaminants or pathogens reported in beverages, or recalls issued regarding beverages. Information stored on a network or within an individual external device 405 may be accessed at a later time, for example if there is a delayed response by the individual user who has consumed a beverage or if there is a later report of a problem by another individual. A external device 405 may be incorporated into another device, such as an individual user's cell phone, PDA, or laptop. A detection device may be configured to communicate with a specific beverage immersate 110 or a class of beverage immersates, for example beverage immersates with a certain orientation or capability.

The external device 405 may include additional instrumentation 435. For example, the additional instrumentation 435 may be configured to be operable with the port 430, and may be configured to enhance communication between the port 430 and the beverage immersate 110. The additional instrumentation, for example, may be one or more type configured to process material from the beverage immersate 110; examples include a fluidic or microfluidic system and/or means of providing additional taggants. For example, where a substance includes advanced glycation endproducts, the additional instrumentation 435 in the external device 405 may be configured to treat salivary fluids with hypochloric acid and examine the treated material with NMR spectroscopy. See Yoon et al., "Characterisation of advanced glycation endproducts in saliva from patients with diabetes mellitus," *Biochem. Biophys Res Comm.*, 323: 377-381 (2004), which is herein incorporated by reference. The additional instrumentation 435 may include a sterilizing unit, for example a UVC or steam emitter configured to reduce microbial contamination on the port 430, beverage immersate 110, or some portion of the external device 405.

An external device 405 may include at least one communication device, such as a reporting device 440 like a display screen, a speaker, or a printer, and may be configured for interaction with a system user through a user interface such as a keyboard interface 415. For example, a communication device may be configured to accept queries or directions from at least one system user, such as an individual person or a computational, network, or robotic user. An external device 405 may comprise multiple modules, for instance a handheld module configured to communicate with a separate component. The external device 405 may be configured as a size able to be held by a human hand, and may be configured to be in communication with the beverage immersate 110, through a port 430, for instance a window or a gas port of a type and configuration able to accept a volatile compound or other chemical. In some embodiments the external device 405 may be configured to be wearable by a user, such as on an arm, waist, or back, and may be incorporated into a watch, armband, belt, waistpack, lumbar pack, or backpack. In some embodiments, the external device 405 and the beverage immersate may be configured to communicate through a wireless connection, such as radio frequency (RF) or other signals. An external device 405 may include a telecommunication device, such as a telecommunication device configured to communicate with a network, such as an area, localized, and/or centralized network. A network may include one or more database, such as but not limited to one or more medical history, including for example, genetic or genomic information, drug use history, allergies, medical diagnoses, or surgical history. The external device 405 may be configured as a portion of a network, which might include as a conductive medium part or all of the body. See, for example, U.S. Pat. No. 6,754,472 to Williams et al., titled "Method and apparatus for transmitting power and data using the human body," which is incorporated herein by reference. The external device 405 may be configured as a portion of a network that is integrated with part or all of a building, such as in a domotic, for instance the MavHome under study at the University of Texas at Arlington. The external device 405 may be configured as a portion of a network configured for selective LED lighting, such as described in International Patent Application No. WO 99/31560 to Mueller et al., titled "Digitally controlled illumination methods and systems" which is herein incorporated by reference. Other components of the system may include a digital processing unit, which may be programmable and may include memory. Other components of the system may include at least one data processor configured to implement logic such as comparison, sorting, reduction, and/or endpoint determination. The system may be configured with a data processor configured to collect and analyze multiple data points in a relative fashion, including either serially or in parallel.

Additionally, any part or all components of the system 400 may be provided in a sterile form and/or the system may include sterile packaging for at least a portion of the system, including the beverage immersate. For example, there may be one or more modules that may be swapped out, removed, or replaced and the newly incorporated components may include sterile packaging prior to incorporation. For example, there may be one or more modules that may be swapped out, removed, or replaced and the removed modules may be placed in sterile packaging prior to further analysis or disposal.

Portions of the system 400 described herein may be configured to be cleaned or have microbial contamination removed, such as before disposal or reuse. For example, the system may be made up of components that are structurally sound after exposure to cleaning or sterilization products or methods. A beverage immersate 110, modules or portions thereof may be configured to be sterilizable through conventional techniques such as UVC exposure, autoclaving or steam cleaning. Similarly, one or more portions of an external device may be configured to be sterilizable. For example, it may be desirable to sterilize a port 430 configured for direct contact with a beverage immersate 110. In some embodiments; the beverage immersate 110 and/or the external device may include UVC capability to self-sterilize. For example, one or more UVC-emitting light source may be incorporated into the beverage immersate 110 and/or the external device, and configured to sterilize the relevant surfaces before use or between uses. Similarly, one or more steam-emitting instruments may be incorporated into the beverage immersate 110 and/or the external device, and configured to clean or eliminate microbes on the relevant surfaces before use, after use, or between uses. FIG. 5 depicts aspects of the systems and methods described herein. As illustrated in FIG. 5A, a beverage immersate 110 is configured to fit within a personal use beverage container 100 holding a fluid 105. A beverage immersate 110 includes at least one sensor, the at least one sensor configured to detect at least one substance in the fluid within a personal use beverage container 100. FIG. 5B illustrates a beverage immersate, such as the one illustrated in FIG. 5A, incorporated into a system including one or more external devices, such as detectors, indicators, user interfaces, and computing devices. As shown in FIG. 5B, an external device may be integrated into a room component or furnishing such as a table, tray, mirror or bar top. An external device may be incorporated into a fitment, such as an integral part of a room or furniture. For example, an external device may be incorporated into shelving, a wall unit, or a cabinet. An external device may be incorporated into a coaster, beverage container frame or base, or similar object. An external device may be a stand-alone device, such as an enclosure or holder for the beverage immersate either alone or within a personal use beverage container. FIG. 5B depicts the beverage immersate 110 located in a personal use beverage container 100 containing a fluid 105, and resting on a table 515. The table 515 includes an integrated detection device. As depicted in FIG. 5B, a detection device incorporated into an object such as a table or bar includes a port 520 configured for communication with the beverage immersate 110, wherein the port 520 is a defined region on the table, tray, or bar top configured to correspond with the beverage immersate 110 in location and size. In some embodiments, the port 520 configured for communication with the beverage immersate 110 may encompass a large region or the entirety of a table, tray, or bar top, and may not be immediately noticeable to a casual observer. In some embodiments, the port 520 configured for communication with the beverage immersate 110 may be incorporated into a coaster, beverage container frame or base, or similar object. As shown in FIG. 5B, an object, such as a table 515, incorporating a detection device with a port 520 configured for communication with the beverage immersate 110, may include an indicator device 525. As depicted in FIG. 5B, an indicator device 525 may include an indicator that displays when a specific substance or class of substances is detected, such as toxins, allergens or substances that may be desirable or undesirable to some users. For example, an indicator device 525 may display a warning sign, a positive sign, lettering, a logo, or another symbol. An indicator device 525 may also, depending on the embodiment, be configured to indicate when the lack of a specific substance or group of substances has been detected, such as a lack of toxins, allergens or substances that may be undesirable to some users. An indicator device 525 may include one or more light displays, for example light displays embedded in the table or bar top, which are configured to switch on in response to a signal from the detection device. In some embodiments, the external device may send and receive communication signals 540 from a separate computing device 530, which may be a portion of a network. For example, the external device and the computing device may communicate via wireless, cable, electronic, IR, auditory or optical signals.

A system user 535, such as a caregiver, medical personnel, bartender, restaurant worker, public health worker or individual user may interact with the external device, computing device 530, additional instrumentation, and/or a detection device, either directly or via a network. A system user 535 may interact with an individual user's PDA, cell phone or computer as part of the system. A "system user" as used herein, includes one or more entities that interact with the beverage immersate system, such as to obtain information from the system or to provide information to the system. Although system user 535 is shown/described herein as a single illustrated figure, those skilled in the art will appreciate that system user 535 may be representative of a human user, a robotic user (e.g., computational entity), and/or substantially any combination thereof (e.g., a user may be assisted by one or more robotic agents) unless context dictates otherwise. A system user may include, for example, a network or group of computing devices. Those skilled in the art will appreciate that, in general, the same may be said of "sender" and/or other entity-oriented terms as such terms are used herein unless context dictates otherwise.

In some embodiments, a beverage immersate may include at least one sensing element. A sensing element may include mechanisms such as a temperature sensor, pH detector, pressure sensor, or time-keeping device. In some embodiments, the release or retention of one or more provided agent, such as a taggant or medicinal agent, may be operably connected to one or more sensing element, such as a taggant reservoir which is triggered to release taggant material at a preset time point or in response to a change in pH detected by the sensing element. In some embodiments, the sensing element may be operably connected to a signal emitter, such as a light or vibration emitting device. In some embodiments, a signal may be generated in response to one or more sensing element, such as a light or vibratory signal that is generated in response to the detection of a temperature, pH or pressure range. In some embodiments, data from one or more sensing element may be transmitted or recorded along with the sensed data, such as when temperature or pH relevant to the sensor is included in information communicated to the detection device, computing device, or network.

Figure 6:
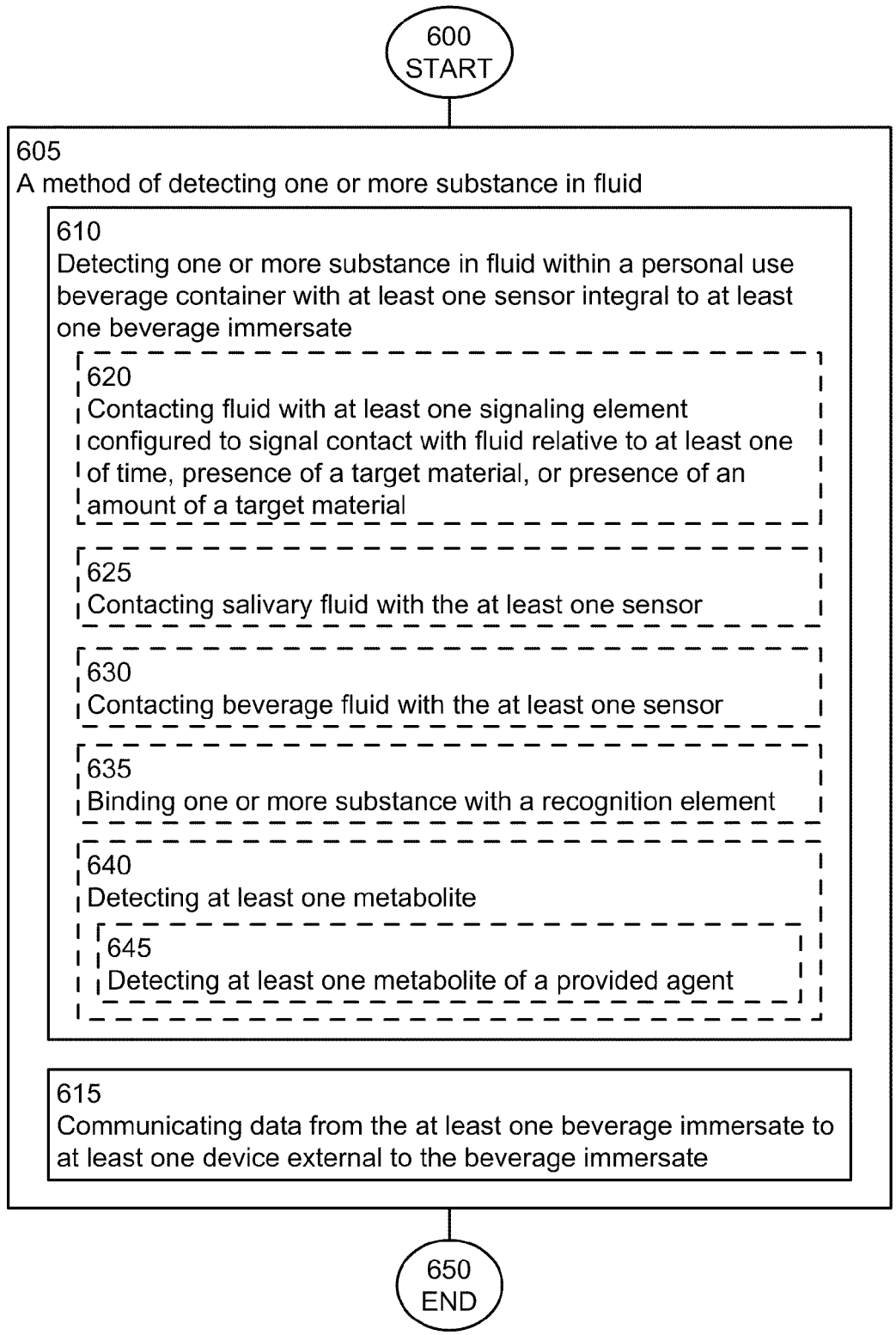
FIG. 6 illustrates a flowchart of a method.

FIG. 6 illustrates a flowchart of a method. The start of the method is depicted as block 600. Block 605 shows a method of detecting one or more substance in fluid. For example, the method may detect one or more substance in beverage fluid. For example, the method may detect one or more substance in a mixture of beverage fluid and salivary fluid in a personal use beverage container. Block 605 contains blocks 610 and 615. Block 610 depicts detecting one or more substance in fluid within a personal use beverage container with at least one sensor integral to at least one beverage immersate. Block 615 illustrates communicating data from the at least one beverage immersate to at least one device external to the beverage immersate. For example, the beverage immersate may communicate wirelessly with a port configured for communication operably attached to an external detection device. For example, a sensor integral to the beverage immersate may emit light which is detectable by an external detection device. For example, a sensor integral to the beverage immersate may emit RF signals which are detectable by an external detection device. For example, the at least one device external to the beverage immersate may be integrated with another item, such as a table, tray, basket, bin, coaster or bar. For example, the at least one device external to the beverage immersate may be integrated with an electronic device, such as a PDA, laptop, or cell phone. The external device may, for example, display some portion of the data to a system user, store the data in memory, transmit the data, and/or record the data in a history or chronicle. Block 650 shows the end of the method. Block 610 may contain one or more of blocks 620, 625, 630, 635, or 640. Block 640 may contain block 645. Block 620 shows contacting fluid with at least one signaling element configured to signal contact with fluid relative to at least one of time, presence of a target material, or presence of an amount of a target material. A signaling element may signal contact with fluid by releasing, for example, at least one of a chromogen, a fluorogen, an ink, a dye, or a flavoring. A signaling element may signal contact with fluid by initiating, for example, vibrations, light, sound, or electric stimulus. Block 625 depicts contacting salivary fluid with the at least one sensor. Block 630 illustrates contacting beverage fluid with the at least one sensor. For example, fluid, which may contain both beverage fluid and salivary fluid, within a personal use beverage container may come into contact with a sensor integral to a beverage immersate within the personal use beverage container. Block 635 shows binding one or more substance with a recognition element. For example, one or more recognition element within a matrix integral to a sensor may bind one or more substance. Block 640 depicts detecting at least one metabolite. Block 645 illustrates detecting at least one metabolite of a provided agent.

Figure 7:
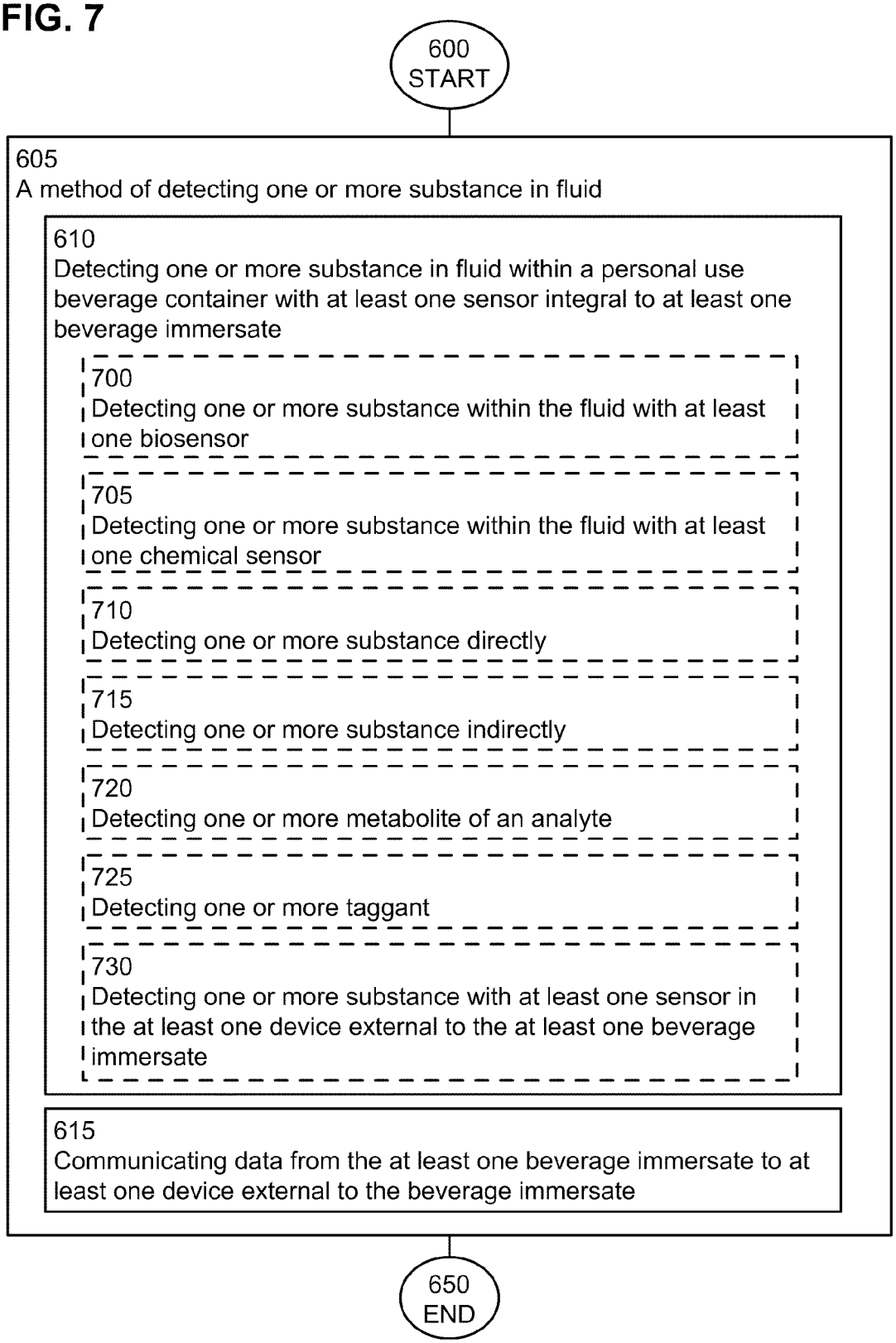
FIG. 7 depicts a flowchart of a method.

FIG. 7 illustrates alternative configurations of the method diagram shown in FIG. 6. Block 610 may include one or more of blocks 700, 705, 710, 715, 720, 725 and 730. Block 700 depicts detecting one or more substance within the fluid with at least one biosensor. Block 705 shows detecting one or more substance within the fluid with at least one chemical sensor. Block 710 illustrates detecting one or more substance directly. Block 715 depicts detecting one or more substance indirectly. Block 720 shows detecting one or more metabolite of an analyte. Block 725 illustrates detecting one or more taggant. Block 730 depicts detecting one or more substance with at least one sensor in the device external to the beverage immersate.

Figure 8:
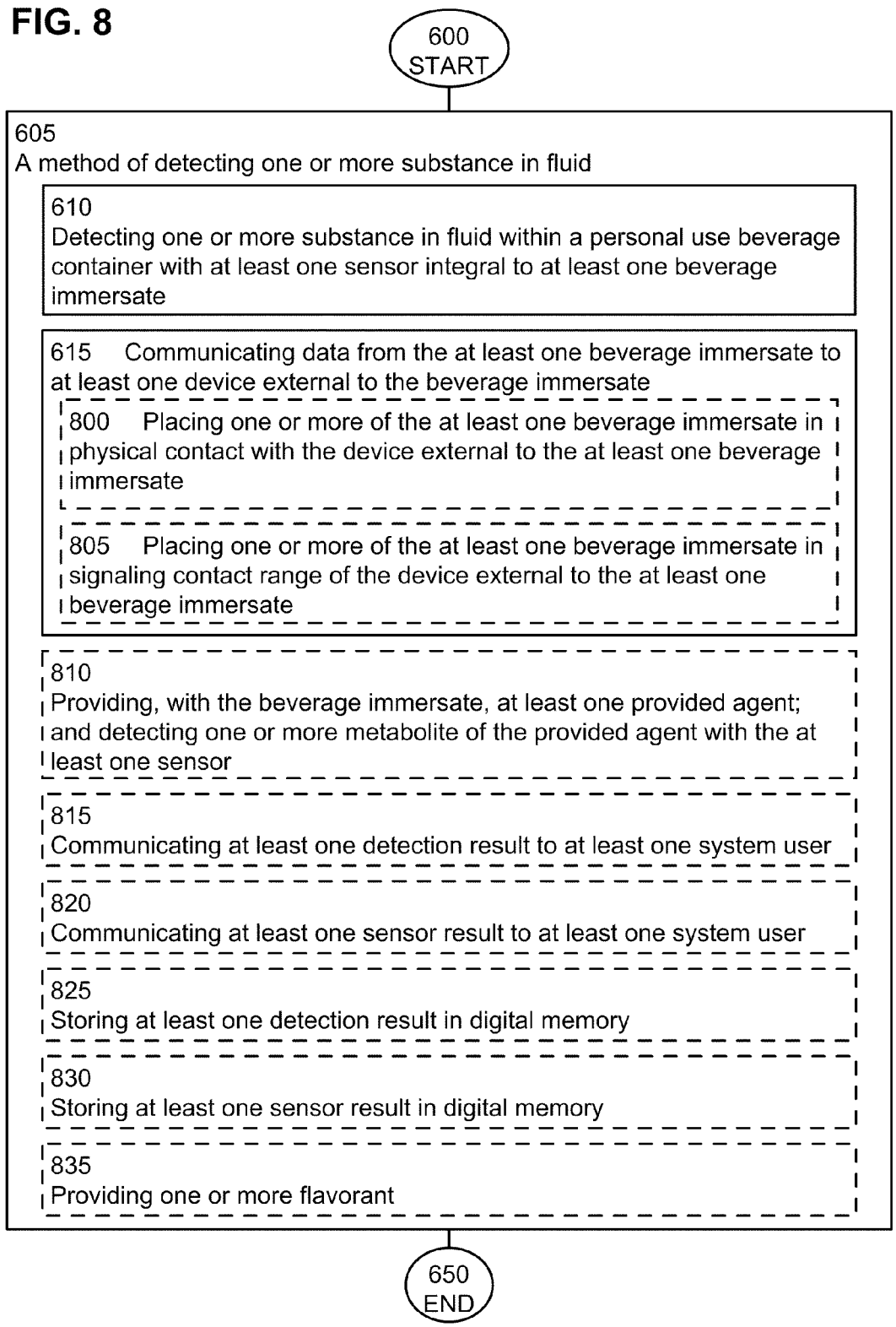
FIG. 8 shows a flowchart of a method.

FIG. 8 illustrates variants of the method diagram shown in FIG. 6. FIG. 8 illustrates that block 615 may include one or more of blocks 800 and 805. Block 615 illustrates communicating data from the at least one beverage immersate to at least one device external to the beverage immersate. Block 800 shows placing one or more of the at least one beverage immersate in physical contact with the device external to the at least one beverage immersate. For example, a beverage immersate may be placed in a port as illustrated as 430 in FIG. 4. Block 805 depicts placing one or more of the at least one beverage immersate in signaling contact range of the device external to the at least one beverage immersate. For example, a beverage immersate located in a fluid within a personal use beverage container may be placed in signaling contact range of an external device that includes a detection device, such as the table depicted as 515 in FIG. 5. As shown in FIG. 8, block 605 may include one or more of blocks 810, 815, 820, 825, 830 and 835. Block 810 illustrates providing, with the beverage immersate, at least one provided agent; and detecting one or more metabolite of the provided agent with the at least one sensor. For example, an agent may be provided with the beverage immersate in an emulsion or encapsulation, or within one or more reservoir. For example, an agent may be released from the beverage immersate into the fluid, ingested by an individual user, and a metabolite of the agent released into the fluid from the individual user's oral cavity. Block 815 shows communicating at least one detection result to at least one system user. For example, a detection result may be indicated on a user interface integral to the detection device. Block 820 depicts communicating at least one sensor result to at least one system user. For example, a beverage immersate may change color or appearance in response to a matrix integral to a sensor binding a substance. Block 825 shows storing at least one detection result in digital memory. Block 830 illustrates storing at least one sensor result in digital memory. Block 835 shows providing one or more flavorant.

Systems and methods as described herein may be used in a variety of ways and for a variety of purposes. The information gained from systems and methods as described herein may be used to determine a state related to environmental exposure, a risk state, or therapeutic response such as to medicine or diet. In addition to the health of a user, the habits and exposure of an individual may be monitored by detecting substances such as controlled substances, pollutants, allergens, ingested substances, inhaled substances, or adsorbed substances. Furthermore, substances indicative of an environmental effect may be detected. Monitoring may be implemented routinely, such as on a daily or weekly schedule, for instance using the same components every day to test, for example, for allergens or contraindicated substances. A specific user may utilize components of the system in an individualized fashion, for example a person wishing to minimize their exposure to a specific substance otherwise not found objectionable by the general public may test their own beverages prior to drinking. For example, a diabetic may monitor glucose in their beverages. For example, ethanol may be monitored in beverages intended for people such as children or individuals contraindicated for ethanol consumption. Or, the system may be utilized including the components in an alternate but routine fashion, replacing part of the system at each use. For instance, each day of the week a different test could be performed for a different substance. Or, an occasional test could be performed as desired, for example to consider possible exposure to infection.

Other aspects of the systems and methods described herein are described in the examples below.

EXAMPLES

Example 1

A beverage immersate system is configured to detect and indicate microbial contamination in a beverage fluid to a user and to a network. A beverage immersate system including an beverage immersate with a sensor, a detection device including a port configured to communicate with the beverage immersate, and a network to receive data from the detection device can detect microbial contaminants in a beverage and indicate to a user and/or a network (including for example, an individual drinking the beverage, caregivers, beverage servers, and beverage sellers) the presence of microbial contaminants.

A beverage immersate, including an outer wall made from a plastic polymer and including an inner cavity with a modular unit including a sensor containing a biosensor, is configured so that the beverage immersate may be placed within a port for communication with an external detection device. A beverage immersate is configured to include a modular biosensor incorporating a silicon chip with a bacterial receptor protein (e.g. translocated intimin receptor ("Tir")) imbedded in the chip, which is coated with a reflective substance, for example silicon dioxide ($SiO_2$). (e.g. see Horner et al, "A proteomic biosensor for enteropathogenic *E. coli*," *Biosensors and Bioelectronics*, 21: 1659-1663 (2006) and U.S. Pat. No. 7,292,349 to Miller, titled "Method for biomolecular sensing and system thereof," which are herein incorporated by reference). Enteropathogenic *E. coli* express a cell surface protein, intimin, that specifically binds to Tir immobilized on the silicon chip. Binding of the *E. coli* effectively changes the coating thickness to afford a change in the destructive interference pattern of reflected light. This change is detectable by reflected interferometry. Recombinant DNA methods for bacterial expression and purification of Tir are described in Horner et al, Ibid. Silicon chips (12 mm×25 mm) with a uniform coating of precisely 1400 Å of $SiO_2$ are derived from silicon wafers (supplied by Silicon Valley Machines, Inc., Los Altos Hills, Calif.) by slow etching in dilute hydrofluoric acid and dicing the wafers. To derivatize the chips, they are coated with (3-aminopropyl)triethoxysilane, reacted with glutaraldehyde, and then reacted with purified Tir protein (e.g. at a concentration of about 500 µM) to covalently attach the Tir protein to the chips via amine groups (see Horner et al, Ibid. for detailed methods).

A beverage immersate including a Tir silicon chip can test a beverage fluid for the presence of enteropathogenic *E. coli*. A sensor that incorporates a biosensor containing a Tir silicon chip functions by binding pathogenic bacteria via their intimin protein; binding alters the reflective properties of the chip. A detection device then detects the changes in the reflective properties via reflected interferometry. A Tir-silicon chip biosensor module is analyzed for the presence of bound bacteria with a detection device containing a reflective interferometry apparatus including: a 1 mW HeNe laser operating at 632.8 nm; a spatial filter; a collimating lens; a polarizer; and a redirecting mirror (all are available from Spectra-Physics Lasers Division, Mountain View, Calif.). Reflected light off of the chip located at a sample stage is captured by a QICAM CCD camera (available from QImaging, Surrey, B.C. Canada). Methods for performing reflected interferometry are given in Horner et al, Ibid and U.S. Pat. No. 7,292,349 ibid. Images are processed with software, including with ImageJ software (see Abramoff et al., "Image processing with ImageJ," *Biophotonics International*, 11: 36-43 (2004) which is herein incorporated by reference). Furthermore, image data can be analyzed and plotted with Origin 7.0 software (available from OriginLab Corp., Northampton, Mass.).

Figure 9:
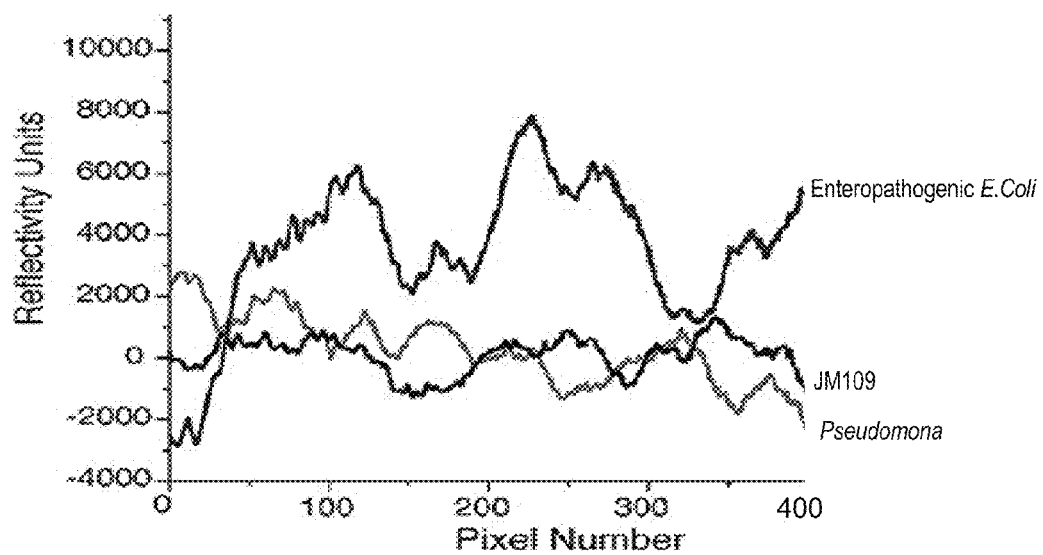
FIG. 9 depicts a graph of reflective signal from Tir-silicon biosensor chips exposed to bacterial cultures.

FIG. 9 illustrates that enteropathogenic *E. coli* grown in liquid culture are detected with a Tir silicon chip by interference reflectivity, while negative control cultures of *E. coli*, JM109 and *Pseudomonas aeruginosa* elicit a baseline response (as shown by Horner et al, Ibid.). FIG. 9 depicts reflective signal from Tir-silicon chips exposed to bacterial cultures. Cultures of Enteropathic *E. coli*, JM109 and *Pseudomonas aeruginosa* were applied to Tir-silicon chips, and reflective signals derived from illumination with a He/Ne laser at 632.8 nm were recorded with a CCD camera. (Adapted from Horner et al, Ibid.) FIG. 9 depicts the resulting reflectivity units on the vertical (X) axis relative to the pixel number on the horizontal (Y) axis for each of the three culture types.

A beverage immersate system including a sensor such as a biosensor module containing a Tir silicon chip, a detection device that measures reflective interferometry, and computer software to process and analyze the images is configured to indicate the presence of enteropathogenic *E. coli*, and other bacteria expressing intimin on their cell surface, in fluids in a personal use beverage container. Information communicated from the detection device to individuals, care providers, food and beverage producers, including via a computer network, can prevent ingestion of contaminated beverages, alert food providers to bacterial contamination and infections, and allow rapid response by food and beverage producers to minimize *E. coli* ingestion by individual users.

Example 2

A beverage immersate system is configured to detect and indicate microbial contamination in beverage fluid to a user and to communicate relevant information to a network. A beverage immersate system including a beverage immersate with a sensor and a detection device including a port configured to communicate with the beverage immersate detects microbial contaminants in beverages and indicates to individuals (including for example, an individual drinking the beverage, caregivers, beverage servers, and beverage sellers) the presence of microbial contaminants. Furthermore, information relating to the detection is communicated to a computer network.

A beverage immersate, including an outer wall made from a plastic polymer and including an inner cavity with a modular unit containing a sensor including a biosensor, is configured so that the modular unit is removable for communication with a detection device. The beverage immersate is configured to detect microbial contamination with a modular unit containing a biosensor that includes an aptamer recognition element configured to bind a biotoxin or microbe. A system including a beverage immersate containing a modular biosensor including an aptamer recognition element configured to bind *E. coli* 0111:B4 and a field effect transistor (FET) device that transduces an electrical signal detectable by the detection device indicates the presence of the microbial contaminant *E. coli* 0111:B4 in a beverage fluid.

Aptamers that recognize microbes with specificity and sensitivity are selected from random oligonucleotide libraries. More specifically, aptamers specific for *E. coli* 0111:B4 are selected from a random oligonucleotide collection by using magnetic beads conjugated with lipopolysaccharide (LPS) 0111:B4 (see Dwarakanath et al, "Quantum dot-antibody and aptamer conjugates shift fluorescence upon binding bacteria," *BBRC* 325: 739-743 (2004) and Bruno and Kiel, "Use of magnetic beads in selection and detection of biotoxin aptamers by electrochemiluminescence and enzymatic methods," *BioTechniques*, 32: 178-183 (2002) which are herein incorporated by reference). The biotoxin LPS O111:B4 (obtained from Sigma-Aldrich, St. Louis, Mo.) is conjugated to Dynal M-270 amine-magnetic beads (available from Invitrogen Corp., Carlsbad, Calif.) using sodium periodate and cyanoborohydride chemistry as described by Dwarakanath et al, Ibid. Methods for construction, selection and amplification of a single stranded, random sequence DNA pool containing approximately $2 \times 10^{14}$ different molecules are described in U.S. Pat. No. 5,631,146 to Szostak et al, titled "DNA aptamers and catalysts that bind adenosine or adenosine-5'-phosphates and methods for isolation thereof," which is herein incorporated by reference. To select aptamers that recognize *E. coli* 0111:B4, the random oligonucleotide sequence pool is incubated with and allowed to bind to LPS 0111:B4-magnetic beads. The aptamer-LPS-magnetic bead complexes are washed three times and then polymerase chain reaction ("PCR") is used to amplify the aptamers bound to the LPS-magnetic beads. PCR reagents, protocols and thermal cyclers are available from Applied Biosystems, Foster City, Calif. Selected and amplified oligonucleotides are added to another aliquot of LPS-magnetic beads and the entire process is repeated four more times (see Bruno et al, Ibid.).

Figure 10:
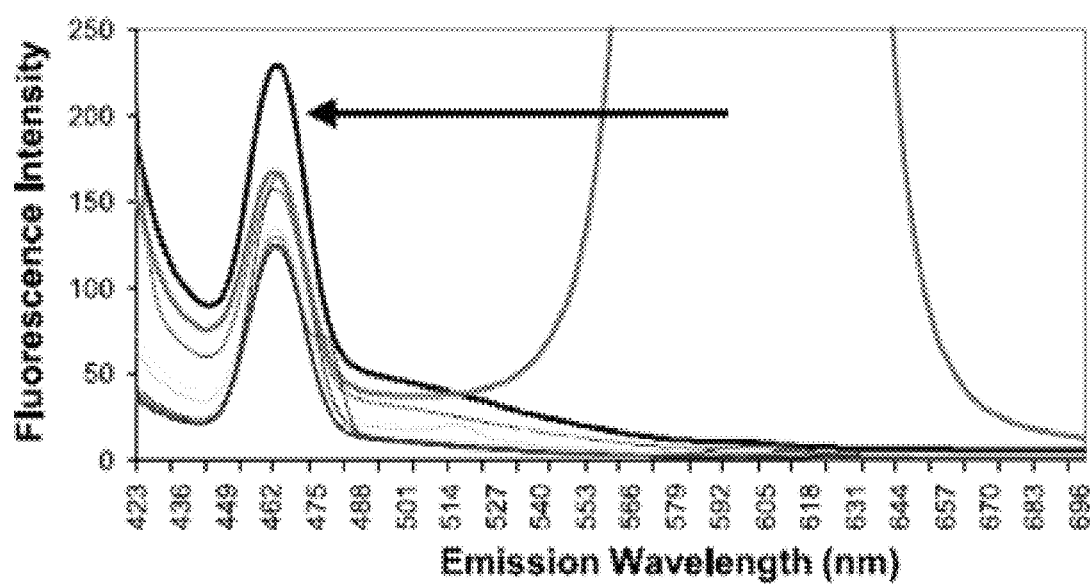
FIG. 10 illustrates detection of fluorescence emission spectra of $E.\ coli$ 0111:B4 with quantum dot aptamers.

Binding of selected aptamers to *E. coli* 0111:B4 is verified by attachment of quantum dots to the aptamers and performance of fluorescence spectroscopy. Quantum dots (also known as nanocrystals) are available from eBioscience, Inc. (San Diego, Calif.). Protocols for attaching quantum dots to oligonucleotides via a N-b-maleimidopropionic acid ("BMPA"; Thermo Fisher Scientific Inc., Rockford, Ill.) linkage are detailed in Dwarakanath et al, Ibid. Selected aptamers with quantum dots attached specifically bind to *E. coli* 0111:B4 (available from American Type Culture Collection, Manassus, Va.), inducing a shift in the fluorescence emission wavelength of the quantum dots (as shown by Dwarakanath et al, Ibid.). FIG. 10 (adapted from Dwarakanath et al., Ibid.) illustrates detection of fluorescence emission spectra of *E. coli* 0111:84 with quantum dot aptamers. The vertical axis indicates detected fluorescence intensity and the horizontal axis indicates emission wavelength in nm. The horizontal arrow indicates the shift in emission wavelength for quantum dot-aptamers bound to *E. coli* versus quantum dot-aptamers alone (i.e. from left to right in the figure). Serial 10-fold dilutions (grey-shaded curves) of an *E. coli* culture (starting at approximately $2.8 \times 10^6$ bacteria per mL (uppermost curve) were combined with quantum dot-aptamers. The arrow indicates the shift in emission wavelength for quantum-dot aptamers alone ($\lambda_{max}$=~605 nm) and quantum dot aptamers plus *E. coli* ($\lambda_{max}$=~462 nm). Excitation was at 400±20 nm. (Adapted from Dwarakanath et al, Ibid.)

Selected aptamers that specifically bind *E. coli* (or other microbes, as indicated for the embodiment) are used to initiate the action of electronic signaling elements in a beverage immersate. In response to *E. coli* detection by specific binding to the aptamer, electronic elements of the beverage immersate such as flashing lights, vibrating or emitting sounds indicates the presence of microbial contaminants. Aptamers that create electronically detectable signals are created by mutagenesis of aptamers followed by conjugation of an oxidation/reduction tag to the mutated aptamer. See Stojanovic et al, "Aptamer-based folding fluorescent sensor for cocaine," *J. Am. Chem. Soc.*, 123: 4928-4931 (2001) and Baker et al, "An electronic, aptamer-based small-molecule sensor for the rapid, label-free detection of cocaine in adulterated samples and biological fluids," *J. Am. Chem. Soc.*, 128: 3138-3139 (2006), which are herein incorporated by reference. Aptamers which signal electronically upon binding a specific target protein are described by Lai et al, "Aptamer-based electrochemical detection of picomolar platelet-derived growth factor directly in blood serum," *Anal. Chem.* 79: 229-233 (2007), which is herein incorporated by reference. Covalent attachment of the electroactive label methylene blue ("MB") to the 3' end of a DNA aptamer specific for a target protein creates an electroactive aptamer that signals via electron transfer when the target (e.g. protein) binds. Methods for covalent attachment of MB to an aptamer using an N-hydroxysuccinimide ester of MB to create a MB-aptamer are described by Lai et al, Ibid.

A specific target protein sensor is constructed by immobilization of the MB-aptamer on gold electrodes. Gold working electrodes (0.88 mm$^2$) are fabricated on a glass plate using standard microfabrication techniques. See Lai et al, "Differential labeling of closely spaced biosensor electrodes via electrochemical lithography," *Langmuir*, 22: 1932-1936 (2006), which is incorporated by reference herein. Aptamer electrodes are analyzed by alternating current voltammetry over the range 0.15 to −0.43 Volt versus Ag/AgCl with a 10 Hz, 25-mV ac potential (as shown by Lai et al, (2007), Ibid.). A platinum wire is used as the counter electrode, and electrochemical potentials are reported versus a Ag/AgCl (3 M KCl) reference electrode. Methods and materials including voltammetry instrumentation and experimental parameters are detailed in Lai et al, (2007), Ibid.

Figure 11:
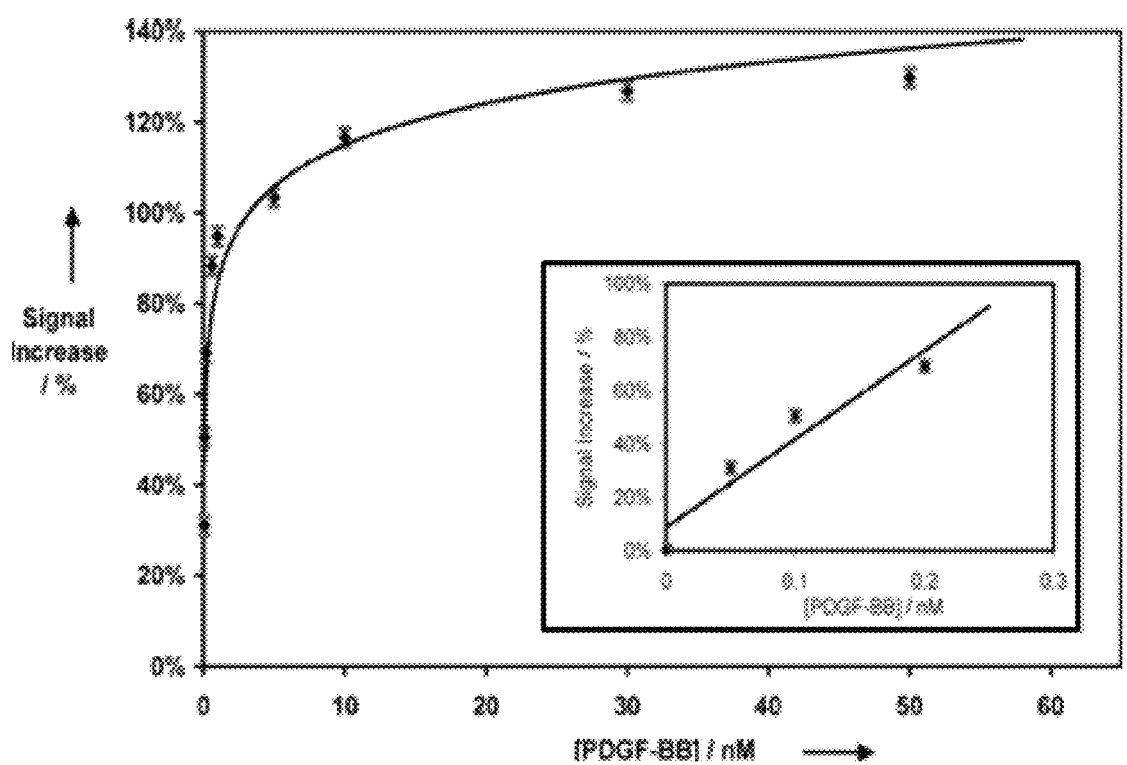
FIG. 11 depicts dose response of PDGF-BB sensor with aptamer-MB.

FIG. 11 illustrates dose response of a sensor containing an aptamer-MB (taken from Lai et al, (2007), Ibid.). A dose-response curve for a target protein (PDGF-BB) sensor based on an aptamer-MB electrode is shown in FIG. 11. The aptamer-modified electrode was analyzed using alternating current voltammetry, and the percent increase in signal (Signal increase/%) is shown on the vertical axis relative to buffer with 0 nanomoles/liter (nM) target protein (PDGF-BB). The horizontal axis illustrates concentration of target protein in nanomoles/liter ([PDGF-BB]/nM). Inset depicts the linear dose response in the 0 to 0.3 nM range of target protein concentration. The measured dynamic range is 50 pM to 10 nM target protein (PDGF-BB). (Adapted from Lai et al, (2007), Ibid.)

Aptamer-MB biosensors are extremely sensitive (e.g. detecting picomolar concentrations of target protein PDGF; see inset FIG. 11) and capable of detecting microbial contaminants or other contaminants in a beverage at very low concentrations. An immersate with an aptamer-modified electrode includes a battery, a direct current/alternating current transformer, a reference electrode (e.g. Ag/AgCl electrode), microcircuitry and signaling elements. As an illustration, FIG. 2B depicts a beverage immersate 110 including signaling elements such as a light emitter 235 and vibration emitter 240. A beverage immersate contains a light emitting diode (LED) configured to illuminate in response to an electronic signal from the aptamer modified electrode in the sensor. Processor-controlled LED systems that control LED illumination based on electronic signals received by the LED system are described in U.S. Pat. No. 6,528,954 titled, "Smart light bulb" issued to Lys and Mueller, which is herein incorporated by reference.

Beverage immersates containing sensors including aptamer-based biosensors can also be configured to signal electronically to external devices and a network. Detection of microbial contaminants in a beverage fluid is indicated to the individual user by LED illumination indicators. Circuitry within the beverage immersate is configured to send a wireless signal to an external device, such as a PDA, computer, or cell phone regarding the detection of the microbial contaminant. Information may also be communicated to a network to alert beverage producers and consumers to the existence of contamination in the beverage fluid. For example, contamination may have arisen from a production process and a beverage producer may be notified that corrective action is required.

Example 3

A beverage immersate system is configured to detect and indicate the presence of toxins, pharmaceuticals, allergens and/or nutrients in beverage and salivary fluids. A beverage immersate system including a sensor configured to detect small molecules (e.g. pesticides) can indicate their presence to an individual user and signal to a public-health or medical network to provide rapid, real-time warnings of toxin exposure. Such a system may be of particular benefit to individuals who are sensitive to pesticides or to those interested in maintaining an organic diet. A beverage immersate configured to detect pesticides in a beverage fluid is constructed from non-toxic polymers, such as polypropylene, and includes a selectively permeable region, an internal cavity, a sensor with recognition elements, a transducer, signal emitters (for example, LED, vibration emitter, or acoustic device), a microprocessor, a microcircuit and a battery. The beverage immersate is part of a system including a detection device with a port configured to communicate with the beverage immersate.

A sensor for pesticides, such as organophosphates, includes a molecularly imprinted polymer as a recognition element, an optical transducer as a transduction element, an electronic transducer, and a releasable taggant. An electrode with a molecularly imprinted polymer that specifically recognizes a small molecule pesticide and transduces an electrical signal in response to the molecular recognition is constructed by layering conducting films and catalytic molecularly imprinted polymers ("MIP"s) onto the surface of an electrode (e.g. gold on glass) as described by Lakshmi et al, "Electrochemical sensor for catechol and dopamine based on a catalytic molecularly imprinted polymer-conducting polymer hybrid recognition element," *Anal. Chem.*, 81: 3576-3584 (2009), which is herein incorporated by reference. An electrochemical sensor for the small molecule catechol is created on a gold electrode (coated on glass) by electropolymerizing a conductive polymer (e.g. N-phenylethylene diamine methacrylamide) onto the gold electrode. A MIP is photochemically attached by activation of the methacrylamide groups of the conductive polymer with N,N'-diethyldithiocarbamic acid benzyl ester (see Lakshmi et al, Ibid.). Methods for creation of MIPs are described in U.S. Pat. No. 7,442,754 B2 to Teppler, titled, "Molecular Imprinting of Small Particles, and Production of Small Particles from Solid State Reactants" and U.S. Pat. No. 7,288,415 B2 to Huang titled "Compositions and Methods for Capturing, Isolating Detecting, Analyzing and Quantifying Macromolecules," which are incorporated herein by reference. A catalytic MIP that recognizes and oxidizes catechol is fabricated by reacting a solution of urocanic acid ethyl ester, catechol (template) and $CuCl_2$ in dimethyl formamide for ten minutes, followed by the addition of ethyleneglycol dimethacrylate.

Figure 12:
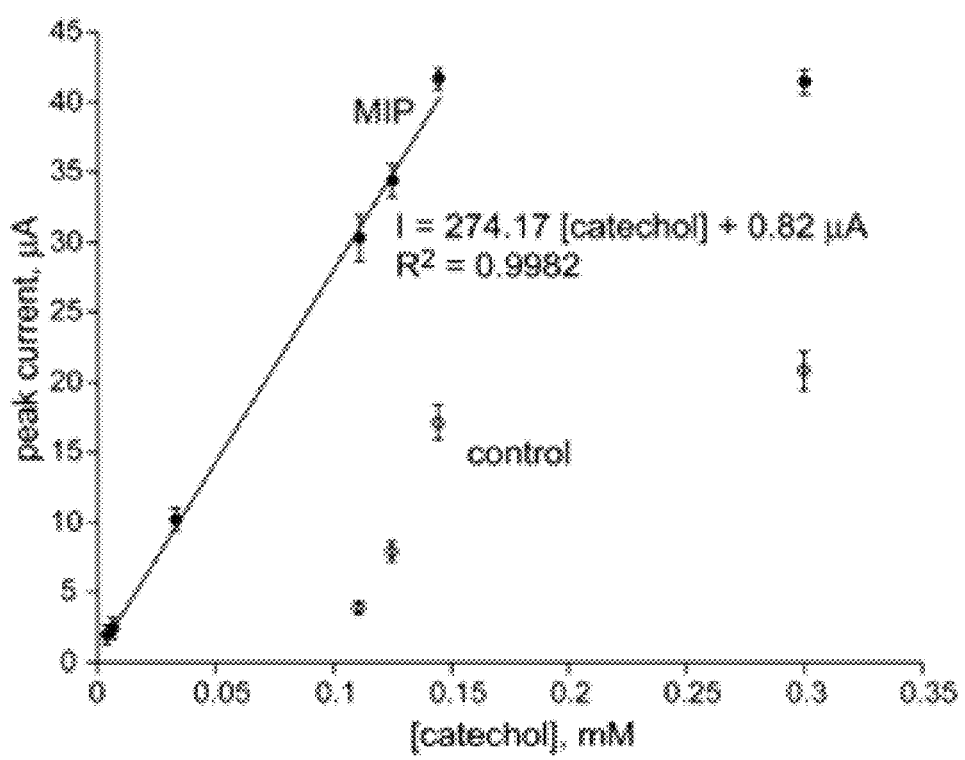
FIG. 12 shows peak current versus catechol concentration for an MIP electrode.

An electrochemical sensor including a MIP selective for catechol, a silver/silver chloride reference electrode and electrical components to perform voltammetry (available from Eco-Chemie BV, Utrecht, Netherlands) detects catechol at concentrations ranging from about 228 nM to 144 µM (see Lakshmi et al, Ibid.). FIG. 12 shows a concentration versus response curve for an electrochemical sensor that detects catechol (taken from Lakshmi et al, Ibid.). The vertical axis illustrates the peak current in microamperes (µA) relative to the horizontal axis, which illustrates the concentration of catechol ([catechol]) in millimoles/liter (mM). The peak current as measured by voltammetry at each concentration of catechol is plotted. Open symbols indicate peak current for a control electrode with a nonimprinted polymer.

The beverage immersate containing an electrochemical sensor including a MIP selective for catechol is configured to detect toxins in a beverage or salivary fluid. An electrical signal from the electrochemical sensor including a MIP selective for catechol is detected by an external detection device through a conductivity or amperometric detector. The detection device then utilizes a microprocessor to analyze the data relative to predetermined calibration curves for the analyte catechol. Electronic signal detectors for analysis of biological fluids are described in U.S. Pat. No. 7,314,453 to Kuo, titled, "Handheld diagnostic device with renewable biosensor," which is herein incorporated by reference. A detection device is configured so that if a minimum or threshold concentration of catechol is detected, the microprocessor illuminates an LED to immediately indicate the presence of catechol to the beverage drinker. The communicated data may be stored in memory on the detection device. The communicated data may be transmitted from the detection device to a computer network, such as to alert public health system users of catechol contamination in the beverage fluid.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. For example, the optical aspects of implementations will typically employ optically-oriented hardware, software, and or firmware.

In some implementations described herein, logic and similar implementations may include software or other control structures. Electronic circuitry, for example, may have one or more paths of electrical current constructed and arranged to implement various functions as described herein. In some implementations, one or more media may be configured to bear a device-detectable implementation when such media hold or transmit a device detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or invoking circuitry for enabling, triggering, coordinating, requesting, or otherwise causing one or more occurrences of virtually any functional operations described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled, implemented, translated, or converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

In a general sense, the various aspects described herein can be implemented, individually and/or collectively, by a wide range of hardware, software, firmware, and/or any combination thereof and can be viewed as being composed in part of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein may be implemented in an analog or digital fashion or some combination thereof.

At least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

The herein described components (e.g., operations), devices, objects, and the discussion accompanying them are used as examples for the sake of conceptual clarity and various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting. The foregoing specific exemplary processes and/or devices and/or technologies are representative of more general processes and/or devices and/or technologies taught elsewhere herein, such as in the claims filed herewith and/or elsewhere in the present application.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

It is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory). A sale of a system or method may likewise occur in a territory even if components of the system or method are located and/or used outside the territory. Further, implementation of at least part of a system for performing a method in one territory does not preclude use of the system in another territory.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

While particular aspects of the present subject matter described herein have been shown and described, it will be apparent that, based upon the teachings herein, changes and modifications may be made without departing from the subject matter described herein and its broader aspects and, therefore, the appended claims are to encompass within their scope all such changes and modifications as are within the true spirit and scope of the subject matter described herein. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). If a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense of the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, recited operations therein may generally be performed in any order. Also, although various operational flows are presented in sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

The various aspects and embodiments disclosed herein are for purposes of illustration and are not intended to be limiting, with the true scope and spirit being indicated by the following claims.

What is claimed is:

1. A beverage immersate comprising:
an immersate body defining at least one beverage immersate, wherein the immersate body defining the at least one beverage immersate includes,
an outer wall sized for immersion in a personal-use beverage container;
at least one sensor on or within the outer wall, the at least one sensor positioned and configured to detect and identify at least one substance in a fluid within a personal use beverage container and generate a signal that the identification has been made;
a reservoir internal to the outer wall of the immersate body, the reservoir positioned and configured to release at least one agent into the fluid within the personal use beverage container; and
at least one signal transmitter positioned and configured to transmit the signal responsive to the at least one sensor.

2. The beverage immersate of claim 1, wherein the at least one sensor comprises:
at least one chemical sensor.

3. The beverage immersate of claim 1, wherein the at least one sensor comprises:
at least one acoustic sensor.

4. The beverage immersate of claim 1, wherein the at least one sensor comprises:
at least one selective medium.

5. The beverage immersate of claim 1, wherein the at least one sensor comprises:
at least one gel.

6. The beverage immersate of claim 1, wherein the at least one sensor comprises:
at least one recognition element configured to identify and bind the at least one substance.

7. The beverage immersate of claim 1, wherein the at least one substance comprises:
an indicator of a physiological state.

8. The beverage immersate of claim 1, wherein the at least one substance comprises:
a metabolite.

9. The beverage immersate of claim 1, wherein the at least one sensor is configured to be indirectly responsive to an analyte.

10. The beverage immersate of claim 1, comprising:
at least one light emitter.

11. The beverage immersate of claim 1, comprising:
at least one signal emitter.

12. The beverage immersate of claim 1, comprising:
at least one reservoir configured for release of at least one medical agent.

13. The beverage immersate of claim 1, comprising:
one or more taggant.

14. The beverage immersate of claim 6, comprising:
an encapsulating material encapsulating the at least one recognition element.

15. The beverage immersate of claim 1, wherein at least a portion of the at least one beverage immersate is dehydrated prior to contact with the fluid.

16. The beverage immersate of claim 1, comprising:
one or more display configured to be responsive to the at least one sensor.

17. A system, comprising:
at least one beverage immersate including,
an immersate body defining the at least one beverage immersate, the immersate body including,
an outer wall sized for immersion in a personal-use beverage container;
at least one sensor on or within the outer wall, the at least one sensor positioned and configured to detect at least one substance in a fluid within a personal use beverage container;
a reservoir internal to the outer wall of the immersate body, the reservoir positioned and configured to release at least one agent into the fluid within the personal use beverage container; and
at least one detection device including at least one port positioned and configured to communicate with the at least one beverage immersate.

18. The system of claim 17, wherein the at least one beverage immersate comprises:
at least one selective medium.

19. The system of claim 17, wherein the at least one beverage immersate comprises:
at least one gel.

20. The system of claim 17, wherein the reservoir is configured to passively release the at least one agent into the fluid over time.

21. The system of claim 17, wherein the reservoir is configured to actively release the at least one agent.

22. The system of claim 17, wherein at least a portion of the at least one beverage immersate is dehydrated prior to contact with the fluid.

23. The system of claim 17, wherein the at least one sensor comprises:
at least one signaling element configured to signal contact with the fluid relative to at least one of time, presence of a target material, or presence of an amount of a target material.

24. The system of claim 17, wherein the reservoir is configured to actively release the at least one agent in response to a signal from the at least one sensor.

25. The system of claim 17, wherein the at least one sensor comprises:
at least one sensor configured to detect at least one substance in beverage fluid.

26. The system of claim 17, wherein the at least one substance comprises:
an indicator of a physiological state.

27. The system of claim 17, wherein the at least one substance comprises:
a metabolite.

28. The system of claim 17, wherein the at least one sensor recognizes one or more substance.

29. The system of claim 17, wherein the at least one sensor comprises:
at least one recognition element.

30. The system of claim 17, wherein the at least one sensor is configured to respond to one or more taggant.

31. The system of claim 17, wherein the at least one sensor is configured to be indirectly responsive to an analyte.

32. The system of claim 17, wherein the at least one detection device is configured to communicate with at least one network.

33. The system of claim 17, wherein the at least one detection device comprises:
a fitment.

34. The system of claim 17, comprising:
at least one light emitter.

35. The system of claim 17, comprising:
at least one vibration emitter.

36. The system of claim 17, comprising:
at least one signal emitter.

37. The system of claim 17, comprising:
at least one user interface.

38. The system of claim 17, comprising:
at least one sensing device.

39. The system of claim 17, comprising:
at least one medicinal agent.

40. A method of detecting one or more substance in fluid comprising:
detecting one or more substance in fluid within a personal use beverage container with at least one sensor integral to at least one beverage immersate including a reservoir, wherein the at least one beverage immersate is disposed in the fluid;
communicating data from the at least one beverage immersate to at least one device external to the at least one beverage immersate; and
releasing at least one agent into the fluid from the reservoir in response to detecting the one or more substance.

41. The method of claim 40, wherein detecting one or more substance in fluid within a personal use beverage container comprises:
contacting beverage fluid with the at least one sensor.

42. The method of claim 40, wherein detecting one or more substance in fluid within a personal use beverage container comprises:
binding one or more substance with a recognition element.

43. The method of claim 40, wherein detecting one or more substance in fluid within a personal use beverage container comprises:
detecting at least one metabolite.

44. The method of claim 40, wherein detecting one or more substance in fluid within a personal use beverage container comprises:
detecting the one or more substance within the fluid with at least one chemical sensor.

45. The method of claim 40, wherein detecting one or more substance in fluid within a personal use beverage container comprises:
detecting the one or more substance directly.

46. The method of claim 40, wherein detecting one or more substance in fluid within a personal use beverage container comprises:
detecting one or more metabolite of an analyte.

47. The method of claim 40, wherein detecting one or more substance in fluid within a personal use beverage container comprises:
detecting one or more taggant.

48. The method of claim 40, wherein detecting one or more substance in fluid within a personal use beverage container comprises:
detecting one or more substance with at least one sensor in the at least one device external to the at least one beverage immersate.

49. The method of claim 40, comprising:
providing, with the beverage immersate, at least one provided agent; and
detecting one or more metabolite of the provided agent with the at least one sensor.

50. The method of claim 40, comprising:
communicating at least one detection result to at least one system user.

51. The method of claim 40, comprising:
communicating at least one sensor result to at least one system user.

52. The method of claim 40, comprising:
storing at least one detection result in digital memory.

53. The method of claim 40, comprising:
storing at least one sensor result in digital memory.

54. The method of claim 40, wherein the at least one agent includes at least one expectorant, bronchodilator, cough suppressant, vasodilator, analgesic, or antiseptic.

* * * * *